United States Patent
McDavid-Arno et al.

(10) Patent No.: US 11,017,058 B1
(45) Date of Patent: May 25, 2021

(54) EXPERT MEDICAL SYSTEM AND METHODS THEREFOR

(71) Applicants: Kwesi McDavid-Arno, New York, NY (US); Charles Edward Hoffler, II, Palmetto Bay, FL (US)

(72) Inventors: Kwesi McDavid-Arno, New York, NY (US); Charles Edward Hoffler, II, Palmetto Bay, FL (US)

( * ) Notice: Subject to any disclaimer, the term of this patent is extended or adjusted under 35 U.S.C. 154(b) by 407 days.

(21) Appl. No.: 15/355,438

(22) Filed: Nov. 18, 2016

Related U.S. Application Data

(60) Provisional application No. 62/257,953, filed on Nov. 20, 2015.

(51) Int. Cl.
*G06F 19/00* (2018.01)
*G06F 16/25* (2019.01)
*G06F 16/22* (2019.01)

(52) U.S. Cl.
CPC ........ *G06F 19/328* (2013.01); *G06F 16/2237* (2019.01); *G06F 16/2264* (2019.01); *G06F 16/258* (2019.01); *G06F 19/325* (2013.01)

(58) Field of Classification Search
CPC .. G06F 19/328; G06F 19/2237; G06F 19/258; G06F 19/2264; G06F 19/325
See application file for complete search history.

(56) References Cited

U.S. PATENT DOCUMENTS 7,392,201 B1 * 6/2008 Binns ..................... G06Q 50/22
705/4

7,437,302 B2   10/2008  Haskell et al.
8,326,651 B2   12/2012  McLaren et al.
8,731,964 B2    5/2014  Miglietta et al.
(Continued)

FOREIGN PATENT DOCUMENTS

WO    WO03036542      5/2003
WO    WO2007084502    7/2007

OTHER PUBLICATIONS

Song and N. V. Marsh, "Anonymous Indexing of Health Conditions for a Similarity Measure," in IEEE Transactions on Information Technology in Biomedicine, vol. 16, No. 4, pp. 737-744, Jul. 2012, doi: 10.1109/TITB.2012.2194717., teaches utilizing normalization and dot product functions for identifying h (Year: 2012).*

*Primary Examiner* — Fonya M Long
*Assistant Examiner* — Anthony Michael Balaj
(74) *Attorney, Agent, or Firm* — Caldwell Intellectual Property

(57) ABSTRACT

A network-based, collaborative, medical expert system and method for its use, the system is adapted to receive patient billing data from a plurality of care providers worldwide, the patient billing data including billing codes and de-identified patient data, the system further comprising an analysis component adapted to transform the billing codes and the patient data into multidimensional vectors and super-vectors, analyze the super-vectors via vector analysis to correlate diagnoses, treatment regimens, and treatment results with ailments of human anatomy, physiology, and psychology, and return a collaborative patient treatment guide to a user interface of at least a subset of the plurality of care providers, based on a continuous real time receipt of patient billing data, transformation of the billing data, and analysis of the super-vectors.

19 Claims, 10 Drawing Sheets

(56) References Cited

U.S. PATENT DOCUMENTS

| | | | |
|---|---|---|---|
| 2006/0101063 A1* | 5/2006 | Schreeder | G06F 19/328 |
| 2008/0046292 A1* | 2/2008 | Myers | G06Q 50/24 |
| | | | 705/3 |
| 2010/0250286 A1* | 9/2010 | Glimp | G06Q 50/24 |
| | | | 705/3 |
| 2012/0197660 A1 | 8/2012 | Prodanovich | |
| 2014/0170608 A1* | 6/2014 | Ting | G09B 19/0092 |
| | | | 434/127 |
| 2014/0200916 A1* | 7/2014 | Chaudhri | G06F 19/328 |
| | | | 705/2 |
| 2014/0278490 A1* | 9/2014 | Namazifar | G16H 50/30 |
| | | | 705/2 |
| 2015/0149208 A1* | 5/2015 | Lynch | G16H 10/60 |
| | | | 705/3 |

\* cited by examiner

Provider ID Vector Example

| Provider ID | Specialty | Subspecialty (Subspecialty 1) | Additional Subspecialty (Subspecialty 2) | Provider Country | Provider State/Province | Provider City | Provider Geographical Sublocation (ie. borough) | Provider Geographical Sublocation 2 | Postal Code |
|---|---|---|---|---|---|---|---|---|---|
| 56564405 | Int Med | None | | USA | New York | Westchester | None | None | 10507 |

FIG. 5B

Time Vector

| Year | Month | Day | Hour | Minute | Time Zone |
|---|---|---|---|---|---|
| 2015 | March | 1 | 9 | 20 | EST |

FIG. 5C

FRACTURE EXAMPLE ICD 9 VECTOR EXAMPLE

| | ICD 9 | Diagnosis | ailment | body part | phys system | impact | Pandemic |
|---|---|---|---|---|---|---|---|
| raw | 813.42 | unspecified fracture of lower end of radius | fracture | Wrist | skeletal | major | 0/1 |
| mapped | 121 | 14 | 22 | 15 | 3 | 1 | 0 |

FIG. 5D

CARPAL TUNNEL ICD 9 VECTOR EXAMPLE

| | ICD 9 | Diagnosis | ailment | body part | phys system | impact | Pandemic |
|---|---|---|---|---|---|---|---|
| raw | 354.0 | Carpal tunnel | peripheral compression neuropathy | Wrist | Neuro | major | 0/1 |
| mapped | 100 | 10 | 12 | 15 | 12 | 1 | 0 |

FIG. 5E

CPT Vector

| Code | Procedure Type | Procedure Type 1 (Invasiveness) | Non Invasive Procedure Type | Surgical Procedure Type 1 (Technique) | Surgical Procedure Type 2 (Invasiveness) | Surgical Procedure Type 3 (impact) | Anatomic Location | Physiologic system | Physiologic system |
|---|---|---|---|---|---|---|---|---|---|
| 71020 | Chest Xray | Non Invasive | Imaging | None | None | None | Thorax | Respiratory | Cardiovascular |

FIG. 5F

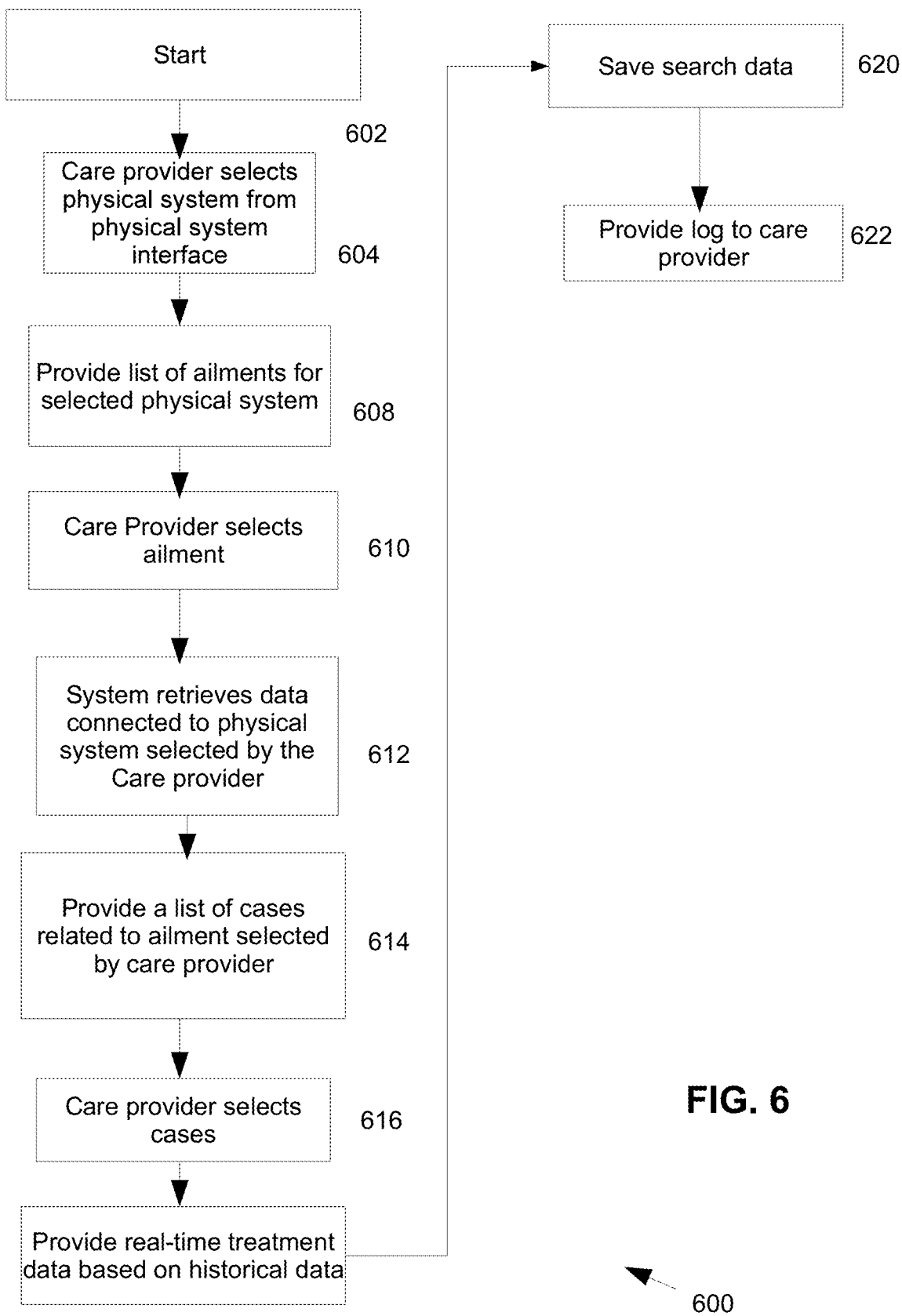

EXPERT MEDICAL SYSTEM AND METHODS THEREFOR

CROSS REFERENCES AND RELATED SUBJECT MATTER

This application is a non-provisional filing of provisional patent application Ser. No. 62/257,953, filed in the United States Patent Office on Nov. 20, 2015, which is incorporated herein by reference in its entirety.

TECHNICAL FIELD

Disclosed are systems and methods directed generally to network systems, and more particularly to, care provider and medical network systems.

BACKGROUND

There is no global medical treatment system where care providers such as Doctors can collaborate to share their experiences in treating various conditions, and the efficacy of such treatment approaches. Care providers largely rely on their personal experience and training, the experience and training of their immediate colleges, or the medical literature. Care providers in practice have access to the outcomes of a small sample of patients, which may or may not be representative of a statistically signifying population.

SUMMARY

The following briefly describes embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed to a Medical Expert System.

In at least one of the various embodiments, the system comprises a processor coupled to a network; memory coupled to the processor; and an analysis component stored in the memory and operable on the processor to: receive patient billing data from a multitude of care providers worldwide; map the patient billing data to an anonymous patient database, the patient billing data including billing codes and de-identified patient data; transform the billing codes and the patient data into multidimensional vectors; and analyze the multidimensional vectors to correlate diagnoses, treatment regimens, and treatment results with ailments of human anatomy, physiology, and psychology.

The system further comprises a transmission component coupled to the processor and adapted to return a real-time, network-based, collaborative patient treatment guide to a user interface of at least a subset of the multitude of care providers, based on a continuous real-time receipt of patient billing data, transformation of the billing data, and analysis of the multidimensional vectors.

In an implementation, the the analysis component is adapted to access an entry of patient billing data having multiple data fields; map each of the data fields to an integer value; and form a multidimensional vector representing the entry of billing data using each integer value of each data field of the entry of billing data to provide a magnitude component and a direction component to the multidimensional vector. In an example, the integer value of a data field is determined based on a diagnostic code or a patient code of the data field.

In an embodiment, the analysis component is adapted to form a super-vector from two or more multidimensional vectors, the super-vector having magnitude and direction components based on the two or more multidimensional vectors. In an example, the analysis component is adapted to analyze multiple super-vectors and to correlate diagnoses, treatment regimens, and treatment results with ailments of human anatomy, physiology, and psychology; and to return the real-time, network-based, collaborative patient treatment guide to at least a subset of the multitude of care providers, based on the correlation.

In at least one of the various embodiments, described is an expert diagnostic system for providing diagnostics over a network, comprising: a network computer, including: a transceiver for communicating over the network; a memory for storing at least instructions; and a processor device that is operative to execute instructions that enable actions, including: mapping patient billing data to an anonymous patient database, the patient billing data including diagnostic codes and de-identified patent data; transforming at least the diagnostic codes and the patient data into data for vector analysis; accepting and processing patient billing data from a patient visit with a care provider into the system, wherein the system is configured to track a plurality of visits for individual patients using the processed billing data, the patient billing data including a timestamp a providerID an ICD-code a CPT-code, a session ID and an obfuscated-individual-identifier; providing a care history for tracked patients; and providing diagnostic data for the tracked patient based on the tracked billing data.

The system can further comprise employing a mapping algorithm to synthesize parametric and non-parametric inputs to create an obfuscating identifier for the patient. The system of can further comprise providing a provider with access to the database to receive diagnostic data in real-time, wherein the system is configured to identify and provide treatment solutions for a de-identified patient via a multidimensional correlation algorithm and employing parametric and non-parametric inputs.

The system can further comprise, in mapping patients and, identifying the most likely mapping, and correcting an anonymous identification based on mapping requirements to determine whether an existing de-identified patient should be selected versus a generating a new de-identified patient.

The system can further comprise: processing diagnosis and billing data into the de-identified patient database, wherein system is configured to allow a user to link diagnoses and successful treatments. In various embodiments, billing and diagnosis data is transformed to create a database that links diagnoses and successful treatments. This transformation leverages large patient volumes and allows decisions to be based massive samples, which can be as large as the entire patient population.

In at least one of the various embodiments, the system can be configured to interact with or include a Medical Trading System.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIGS. 5A-5F represents a logical architecture for a healthcare system in accordance with at least one of the various embodiments;

FIG. 6 illustrates an overview flowchart for a process in accordance with at least one of the various embodiments;

DETAILED DESCRIPTION OF THE EMBODIMENTS

Figure 1:
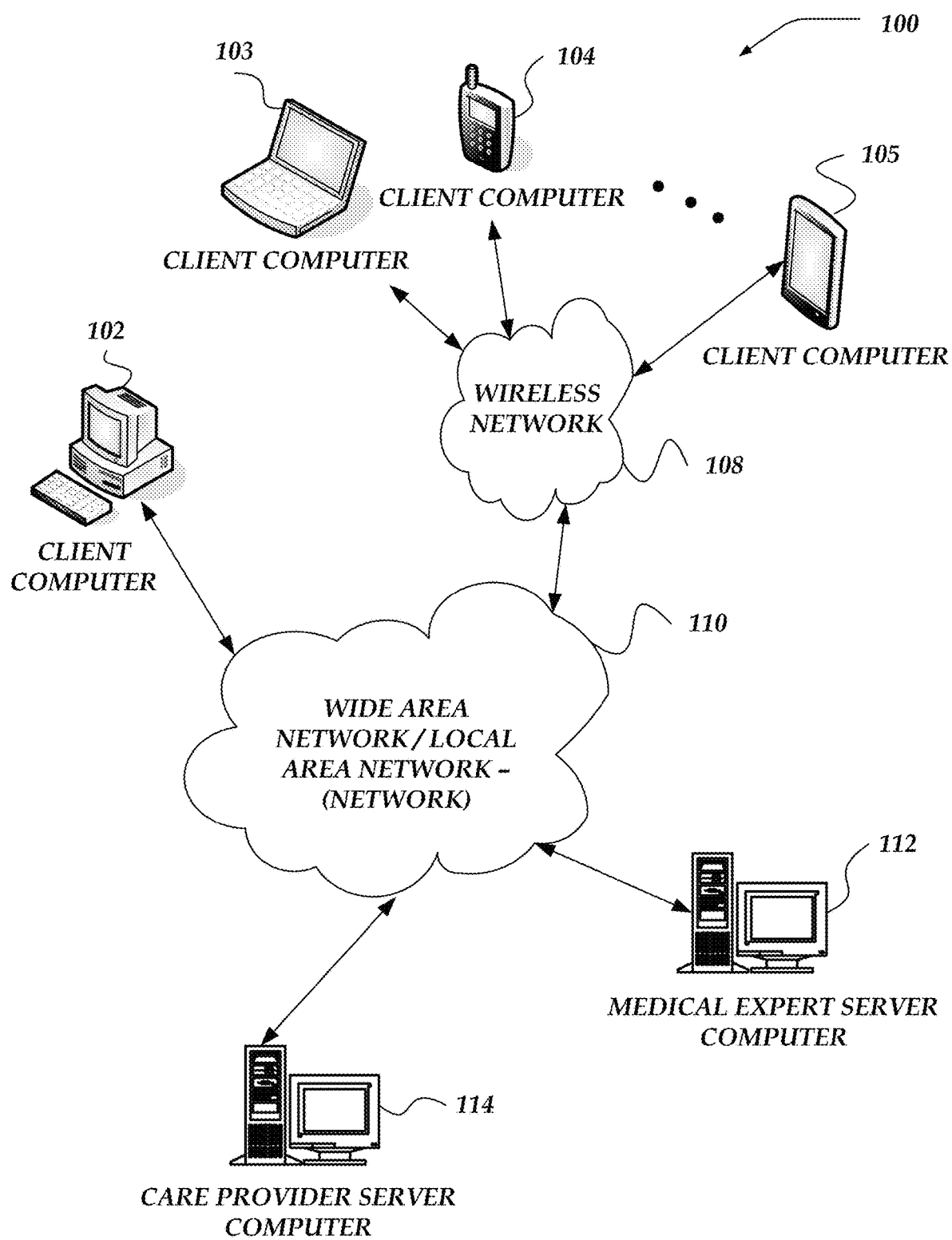
FIG. 1 is a system diagram of an environment in which at least one of the various embodiments may be implemented.

Various embodiments now will be described more fully hereinafter with reference to the accompanying drawings, which form a part hereof, and which show, by way of illustration, specific embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media, or devices. Accordingly, the various embodiments may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The term "herein" refers to the specification, claims, and drawings associated with the current application. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "widget controller" refers to a computer program that may be operative on a client application. Widget controllers may be downloaded and/or otherwise deployed to a client application. Widget controllers may be arranged to be operative for downloading content, monitoring care provider or user actions, or otherwise managing widgets located within client applications.

As used herein, the term "widget" refers to a user-interface element located in the client application. Widgets may be invisible or visible to users of the client applications. In some cases, a widget controller may generate widget "on-the-fly" before deploying content into the widget. Widgets may be adapted to reflect the operating environment of the client application that they are being hosted within. For example, in clients that support HTML, CSS a widget may be an HTML element such as a DIV, P, or the like. For client application operative in a Java environment, a widget may be a View object or Window object, and so on.

As used herein, the term "Host" may refer to an individual person, partnership, organization, or corporate entity that may own or operate one or more digital media properties (e.g., web sites, mobile applications, or the like). Hosts may arrange digital media properties to use hyper-local targeting by arranging the property to integrate with widget controllers, medical expert servers, or provider servers.

Illustrative Operating Environment

FIG. 1 shows components of one embodiment of an environment in which embodiments of the innovations described herein may be practiced. Not all of the components may be required to practice the innovations, and variations in the arrangement and type of the components may be made without departing from the spirit or scope of the innovations. As shown, system 100 of FIG. 1 includes local area networks (LANs)/wide area networks (WANs)-(network) 110, wireless network 108, client computers 102-105, Medical Expert Server Computer 112, and Provider Server Computer 114.

At least one embodiment of client computers 102-105 is described in more detail below in conjunction with FIG. 2. In various implementations, the term "processor" may be used interchangeably for the term "computer," which may refer to any of various computing devices described herein. In one embodiment, at least some of client computers 102-105 may operate over a wired and/or wireless network, such as networks 110 and/or 108. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, an accounting server, a production server, an inventory server, a care provider server, or the like. However, client computers 102-105 are not constrained to these services and may also be employed, for example, as an end-user computing node, in other embodiments. It should be recognized that more or less client computers may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable personal computer capable of connecting to another computing device and receiving information such as, laptop computer 103, smartphone 104, and tablet computers 105, and the like. However, portable computers are not so limited and may also include other portable devices such as cellular telephones, display pagers, radio frequency (RF) devices, infrared (IR) devices, Personal Digital Assistants (PDAs), handheld computers, wearable computers, integrated devices combining one or more of the preceding devices, and the like. As such, client computers 102-105 typically range widely in terms of capabilities and features. Moreover, client computers 102-105 may access various computing applications, including a browser, or other web-based application.

A web-enabled client computer may include a browser application that is configured to receive and to send web pages, web-based messages, and the like. The browser application may be configured to receive and display graphics, text, multimedia, and the like, employing virtually any web-based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), and the like, to display and send a message. In one embodiment, a user of the client computer may employ the browser application to perform various activities over a network (online). However, another application may also be used to perform various online activities.

Client computers 102-105 may also include at least one other client application that is configured to receive and/or send content with another computer. The client application may include a capability to send and/or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), or other device identifier. Such information may be provided in a network packet, or the like, sent between other client computers, Medical Expert Server Computer 112, Provider Server Computer 114, or other computers.

Client computers 102-105 may further be configured to include a client application that enables an end-user to log into an end-user account that may be managed by another computer, such as Medical Expert Server Computer 112, Provider Server Computer 114, or the like. Such end-user account, in one non-limiting example, may be configured to enable the end-user to manage one or more online activities, including in one non-limiting example, search activities, social networking activities, browse various websites, communicate with other users, or the like. However, participation in such online activities may also be performed without logging into the end-user account.

Wireless network 108 is configured to couple client computers 103-105 and its components with network 110. Wireless network 108 may include any of a variety of wireless sub-networks that may further overlay stand-alone ad-hoc networks, and the like, to provide an infrastructure-oriented connection for client computers 103-105. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile devices, such as client computers 103-105 with various degrees of mobility. In one non-limiting example, wireless network 108 may enable a radio connection through a radio network access such as Global System for Mobil communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 103-105 and another computer, network, and the like.

Network 110 is configured to couple network computers with other computers and/or computing devices, including, Medical Expert Server Computer 112, Provider Server Computer 114, client computer 102, and client computers 103-105 through wireless network 108. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, and/or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information of an Internet Protocol (IP). In essence, network 110 includes any communication method by which information may travel between computing devices.

Additionally, communication media typically embodies computer readable instructions, data structures, program modules, or other transport mechanism and includes any information delivery media. By way of example, communication media includes wired media such as twisted pair, coaxial cable, fiber optics, wave guides, and other wired media and wireless media such as acoustic, RF, infrared, and other wireless media.

One embodiment of Medical Expert Server Computer 112 is described in more detail below in conjunction with FIG. 3. Briefly, however, Medical Expert Server Computer 112 includes virtually any network computer capable of vector and super vector analysis, patient tracking, trading and social networking, and treatment interfaces as described herein. Computers that may be arranged to operate as Medical Expert Server Computer 112 include various network computers, including, but not limited to personal computers, desktop computers, multiprocessor systems, microprocessor-based or programmable consumer electronics, network PCs, server computers, network appliances, and the like.

Although FIG. 1 illustrates Medical Expert Server Computer 112 as a single computer, the invention is not so limited. For example, one or more functions of the Medical Expert Server Computer 112 may be distributed across one or more distinct network computers. Moreover, Medical Expert Server Computer 112 is not limited to a particular configuration. Thus, in one embodiment, Medical Expert Server Computer 112 may contain a plurality of network computers. In another embodiment, Medical Expert Server Computer 112 may contain a plurality of network computers that operate using a master/slave approach, where one of the plurality of network computers of Medical Expert Server Computer 112 is operative to manage and/or otherwise coordinate operations of the other network computers. In other embodiments, the Medical Expert Server Computer 112 may operate as a plurality of network computers arranged in a cluster architecture, a peer-to-peer architecture, and/or even within a cloud architecture. Thus, the invention is not to be construed as being limited to a single environment, and other configurations, and architectures are also envisaged.

One embodiment of Provider Server Computer 114 is described in more detail below in conjunction with FIG. 3. Briefly, however, Provider Server Computer 114 includes virtually any network computer capable of computer services for care providers. Computers that may be arranged to operate as Provider Server Computer 114 include various network computers, including, but not limited to personal computers, desktop computers, multiprocessor systems, microprocessor-based or programmable consumer electronics, network PCs, server computers, network appliances, and the like.

Although FIG. 1 illustrates Provider Server Computer 114 as a single computer, the various embodiments are not so limited. For example, one or more functions of the Provider Server Computer 114 may be distributed across one or more distinct network computers. Moreover, Provider Server Computer 114 is not limited to a particular configuration. Thus, in one embodiment, Provider Server Computer 114 may contain a plurality of network computers. In another embodiment, Provider Server Computer 114 may contain a plurality of network computers that operate using a master/slave approach, where one of the plurality of network computers of Provider Server Computer 114 operates to manage and/or otherwise coordinate operations of the other network computers. In other embodiments, the Provider Server Computer 114 may operate as a plurality of network computers within a cluster architecture, a peer-to-peer architecture, and/or even within a cloud architecture. Thus, the invention is not to be construed as being limited to a single environment, and other configurations, and architectures are also envisaged.

Illustrative Client Computer

Figure 2:
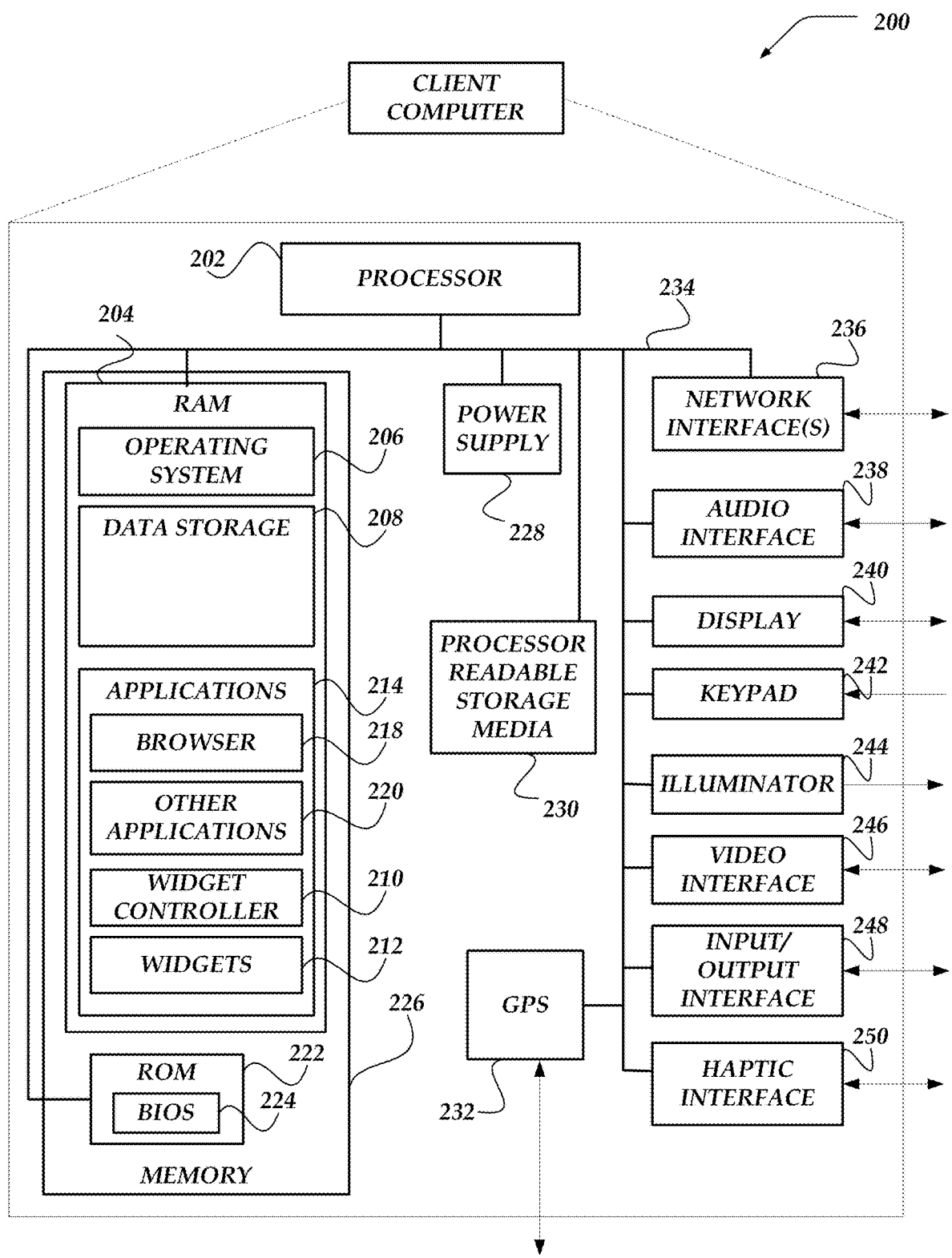
FIG. 2 shows an embodiment of a client computer that may be included in a system such as that shown in FIG. 1.

FIG. 2 shows one embodiment of Client Computer 200 that may be included in a system implementing embodiments of the invention. Client Computer 200 may include many more or less components than those shown in FIG. 2. However, the components shown are sufficient to disclose an illustrative embodiment for practicing the present invention. Client Computer 200 may represent, for example, one embodiment of at least one of Client Computers 102-105 of FIG. 1.

As shown in the figure, Client Computer 200 includes a processor 202 in communication with a mass memory 226 via a bus 234. In some embodiments, processor 202 may include one or more central processing units (CPU). Client Computer 200 also includes a power supply 228, one or more network interfaces 236, an audio interface 238, a display 240, a keypad 242, an illuminator 244, a video interface 246, an input/output interface 248, a haptic interface 250, and a global positioning system (GPS) receiver 232.

Power supply 228 provides power to Client Computer 200. A rechargeable or non-rechargeable battery may be used to provide power. The power may also be provided by an external power source, such as an alternating current (AC) adapter or a powered docking cradle that supplements and/or recharges a battery.

Client Computer 200 may optionally communicate with a base station (not shown), or directly with another computer. Network interface 236 includes circuitry for coupling Client Computer 200 to one or more networks, and is constructed for use with one or more communication protocols and technologies including, but not limited to, GSM, CDMA, TDMA, GPRS, EDGE, WCDMA, HSDPA, LTE, user datagram protocol (UDP), transmission control protocol/Internet protocol (TCP/IP), short message service (SMS), WAP, ultra-wide band (UWB), IEEE 802.16 Worldwide Interoperability for Microwave Access (WiMax), session initiated protocol/real-time transport protocol (SIP/RTP), or any of a variety of other wireless communication protocols. Network interface 236 is sometimes known as a transceiver, transceiving device, or network interface card (NIC).

Audio interface 238 is arranged to produce and receive audio signals such as the sound of a human voice. For example, audio interface 238 may be coupled to a speaker and microphone (not shown) to enable telecommunication with others and/or generate an audio acknowledgement for some action.

Display 240 may be a liquid crystal display (LCD), gas plasma, light emitting diode (LED), organic LED, or any other type of display used with a computer. Display 240 may also include a touch sensitive screen arranged to receive input from an object such as a stylus or a digit from a human hand.

Keypad 242 may comprise any input device arranged to receive input from a user. For example, keypad 242 may include a push button numeric dial, or a keyboard. Keypad 242 may also include command buttons that are associated with selecting and sending images.

Illuminator 244 may provide a status indication and/or provide light. Illuminator 244 may remain active for specific periods of time or in response to events. For example, when illuminator 244 is active, it may backlight the buttons on keypad 242 and stay on while the Client Computer is powered. Also, illuminator 244 may backlight these buttons in various patterns when particular actions are performed, such as dialing another client computer. Illuminator 244 may also cause light sources positioned within a transparent or translucent case of the client computer to illuminate in response to actions.

Video interface 246 is arranged to capture video images, such as a still photo, a video segment, an infrared video, or the like. For example, video interface 246 may be coupled to a digital video camera, a web-camera, or the like. Video interface 246 may comprise a lens, an image sensor, and other electronics. Image sensors may include a complementary metal-oxide-semiconductor (CMOS) integrated circuit, charge-coupled device (CCD), or any other integrated circuit for sensing light.

Client computer 200 also comprises input/output interface 248 for communicating with external devices, such as a headset, or other input or output devices not shown in FIG. 2. Input/output interface 248 can utilize one or more communication technologies, such as USB, infrared, Bluetooth™, or the like.

Haptic interface 250 is arranged to provide tactile feedback to a user of the client computer. For example, the haptic interface 250 may be employed to vibrate client computer 200 in a particular way when another user of a computing computer is calling. In some embodiments, haptic interface 250 may be optional.

Client computer 200 may also include GPS transceiver 232 to determine the physical coordinates of client computer 200 on the surface of the Earth. GPS transceiver 232, in some embodiments, may be optional. GPS transceiver 232 typically outputs a location as latitude and longitude values. However, GPS transceiver 232 can also employ other geo-positioning mechanisms, including, but not limited to, tri-angulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 232 can determine a physical location within millimeters for client computer 200; and in other cases, the determined physical location may be less precise, such as within a meter or significantly greater distances. In one embodiment, however, client computer 200 may through other components, provide other information that may be employed to determine a physical location of the computer, including for example, a Media Access Control (MAC) address, IP address, or the like.

Mass memory 226 includes a Random Access Memory (RAM) 204, a Read-only Memory (ROM) 222, and other storage means. Mass memory 226 illustrates an example of computer readable storage media (devices) for storage of information such as computer readable instructions, data structures, program modules or other data. Mass memory 226 stores a basic input/output system (BIOS) 224 for controlling low-level operation of client computer 200. The mass memory also stores an operating system 206 for controlling the operation of client computer 200. It will be appreciated that this component may include a general-purpose operating system such as a version of UNIX, or LINUX™, or a specialized client communication operating system such as Microsoft Corporation's Windows Mobile™, Apple Corporation's iOS™, Google Corporation's Android™ or the Symbian® operating system. The operating system may include, or interface with a Java virtual machine module that enables control of hardware components and/or operating system operations via Java application programs.

Mass memory 226 further includes one or more data storage 208, which can be utilized by client computer 200 to store, among other things, applications 214 and/or other data. For example, data storage 208 may also be employed to store information that describes various capabilities of client computer 200. The information may then be provided to another computer based on any of a variety of events, including being sent as part of a header during a communication, sent upon request, or the like. Data storage 208 may also be employed to store social networking information including address books, buddy lists, aliases, user profile information, or the like. Further, data storage 208 may also store message, we page content, or any of a variety of user generated content. At least a portion of the information may also be stored on another component of client computer 200, including, but not limited to processor readable storage media 230, a disk drive or other computer readable storage devices (not shown) within client computer 200.

Processor readable storage media 230 may include volatile, nonvolatile, removable, and non-removable media implemented in any method or technology for storage of information, such as computer- or processor-readable instructions, data structures, program modules, or other data. Examples of computer readable storage media include RAM, ROM, Electrically Erasable Programmable Read-only Memory (EEPROM), flash memory or other memory technology, Compact Disc Read-only Memory (CD-ROM), digital versatile disks (DVD) or other optical storage, magnetic cassettes, magnetic tape, magnetic disk storage or other magnetic storage devices, or any other physical medium which can be used to store the desired information and which can be accessed by a computer. Processor readable storage media 230 may also be referred to herein as computer readable storage media and/or computer readable storage device.

Applications 214 may include computer executable instructions which, when executed by client computer 200, transmit, receive, and/or otherwise process network data. Network data may include, but is not limited to, messages (e.g. SMS, Multimedia Message Service (MMS), instant message (IM), email, and/or other messages), audio, video, and enable telecommunication with another user of another client computer. Applications 214 may include, for example, browser 218, and other applications 220. Other applications 220 may include, but are not limited to, calendars, search programs, email clients, IM applications, SMS applications, voice over Internet Protocol (VOIP) applications, contact managers, task managers, transcoders, database programs, word processing programs, security applications, spreadsheet programs, games, search programs, and so forth.

Browser 218 may include virtually any application configured to receive and display graphics, text, multimedia, messages, and the like, employing virtually any web based language. In one embodiment, the browser application is enabled to employ HDML, WML, WMLScript, JavaScript, SGML, HTML, XML, and the like, to display and send a message. However, any of a variety of other web-based programming languages may be employed. In one embodiment, browser 218 may enable a user of client computer 200 to communicate with another network computer, such as Medical Expert Server Computer 112 and/or Provider Server Computer 114 of FIG. 1.

Applications 214 may also include Widget Controller 210 and one or more Widgets 212. Widgets 212 may be collections of content provided to the client computer by Medical Expert Server Computer 112. Widget Controller 210 may be a program that may be provided to the client computer by Medical Expert Server Computer 112. Widget Controller 210 and Widgets 212 may run as native client computer applications or they may run in Browser 218 as web browser based applications. Also, Widget Controller 210 and Widgets 212 may be arranged to run as native applications or web browser applications, or combination thereof.

Illustrative Network Computer

Figure 3:
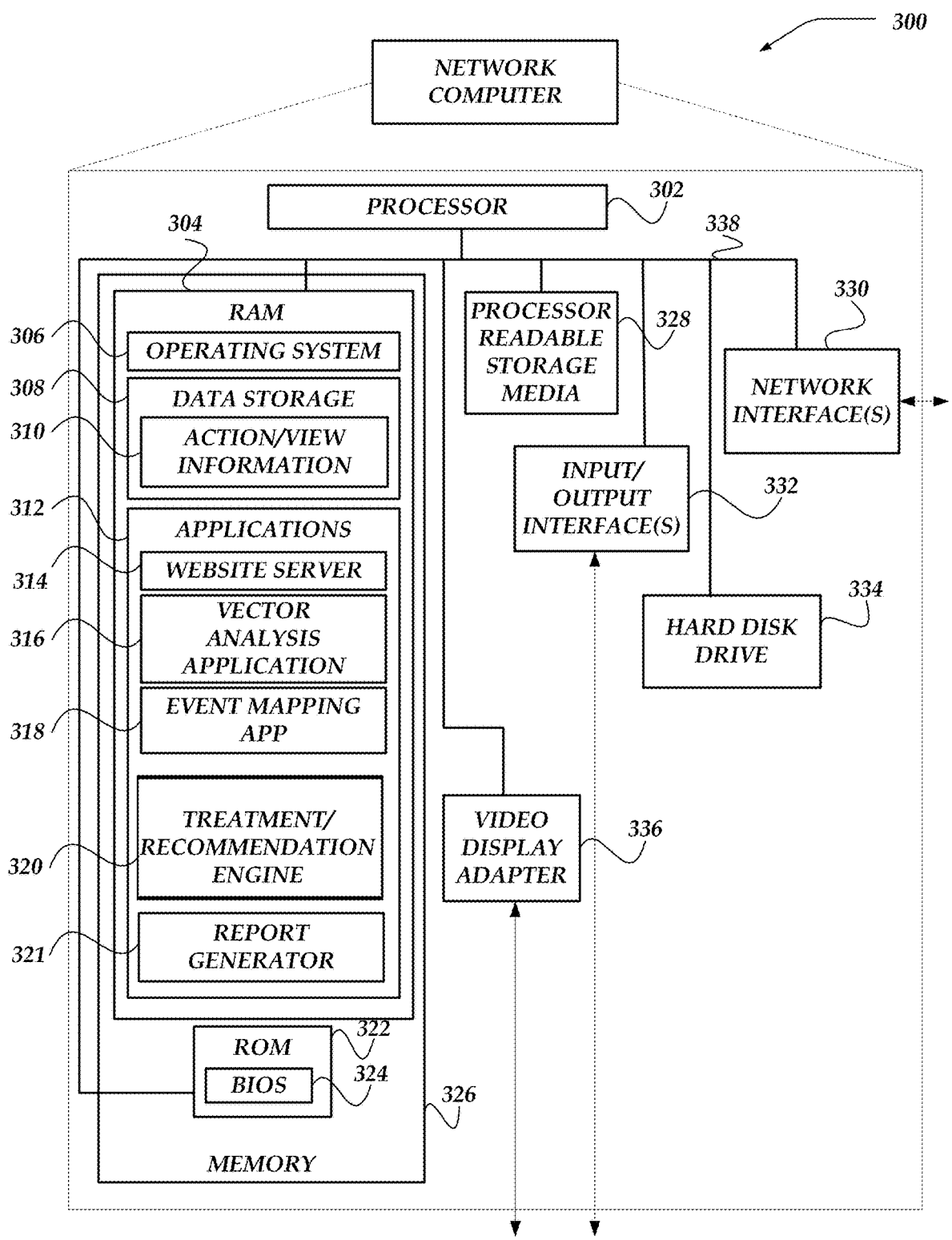
FIG. 3 shows an embodiment of a network computer that may be included in a system such as that shown in FIG. 1.

FIG. 3 shows one embodiment of a network computer 300, according to one embodiment of the invention. Network computer 300 may include many more or less components than those shown. The components shown, however, are sufficient to disclose an illustrative embodiment for practicing the invention. Network computer 300 may be configured to operate as a server, client, peer, a host, or any other computer. Network computer 300 may represent, for example Medical Expert Server Computer 112 and/or Provider Server Computer 114 of FIG. 1, a Medical Trading Server and/or other network computers.

Network computer 300 includes processor 302, processor readable storage media 328, network interface unit 330, an input/output interface 332, hard disk drive 334, video display adapter 336, and memory 326, all in communication with each other via bus 338. In some embodiments, processor 302 may include one or more central processing units.

As illustrated in FIG. 3, network computer 300 also can communicate with the Internet, or some other communications network, via network interface unit 330, which is constructed for use with various communication protocols including the TCP/IP protocol. Network interface unit 330 is sometimes known as a transceiver, transceiving device, or network interface card (NIC).

Network computer 300 also comprises input/output interface 332 for communicating with external devices, such as a keyboard, or other input or output devices not shown in FIG. 3. Input/output interface 332 can utilize one or more communication technologies, such as USB, infrared, Bluetooth™, or the like.

Memory 326 generally includes RAM 304, ROM 322 and one or more permanent mass storage devices, such as hard disk drive 334, tape drive, optical drive, and/or floppy disk drive. Memory 326 stores operating system 306 for controlling the operation of network computer 300. Any general-purpose operating system may be employed. Basic input/output system (BIOS) 324 is also provided for controlling the low-level operation of network computer 300.

Although illustrated separately, memory 326 may include processor readable storage media 328. Processor readable storage media 328 may be referred to and/or include computer readable media, computer readable storage media, and/or processor readable storage device. Processor readable storage media 328 may include volatile, nonvolatile, removable, and non-removable media implemented in any method or technology for storage of information, such as computer readable instructions, data structures, program modules, or other data. Examples of processor readable storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other media which can be used to store the desired information and which can be accessed by a computer.

Memory 326 further includes one or more data storage 308, which can be utilized by network computer 300 to store, among other things, applications 314 and/or other data such as content 310. For example, data storage 308 may also be employed to store information that describes various capabilities of network computer 300. The information may then be provided to another computer based on any of a variety of events, including being sent as part of a header during a communication, sent upon request, or the like. Data storage 308 may also be employed to store messages, web page content, or the like. At least a portion of the information may also be stored on another component of network computer 300, including, but not limited to processor readable storage media 328, hard disk drive 334, or other computer readable storage medias (not shown) within client computer 300.

Data storage 308 may include a database, text, spreadsheet, folder, file, or the like, that may be configured to maintain and store user account identifiers, user profiles, email addresses, IM addresses, and/or other network addresses; or the like.

In at least one of the various embodiments, Data storage 308 may include action/view information 310, which may contain information determined from one or more events for one or more care providers. Action/View Information 310 may include historical information for a care provider and patient visits as well as comparison information based on some or all of the care providers and patients that may be associated with the system.

Data storage 308 may further include program code, data, algorithms, and the like, for use by a processor, such as processor 302 to execute and perform actions. In one embodiment, at least some of data store 308 might also be stored on another component of network computer 300, including, but not limited to processor-readable storage media 328, hard disk drive 334, or the like.

Applications 312 may include computer executable instructions, which may be loaded into mass memory and run on operating system 306. Examples of application programs 312 may include transcoders, schedulers, calendars, database programs, word processing programs, Hypertext Transfer Protocol (HTTP) programs, customizable user interface programs, IPSec applications, encryption programs, security programs, SMS message servers, IM message servers, email servers, account managers, and so forth. In an embodiment, application programs 312 include an analysis component of the Expert Medical Server 112.

Website server 314 may represents any of a variety of information and services that are configured to provide content, including messages, over a network to another computer. Thus, website server 314 can include, for example, a web server, a File Transfer Protocol (FTP) server, a database server, a content server, or the like. Website server 314 may provide the content including messages over the network using any of a variety of formats including, but not limited to WAP, HDML, WML, SGML, HTML, XML, Compact HTML (cHTML), Extensible HTML (xHTML), or the like.

With respect to a Medical Expert Server 112, Applications 312 (e.g., including "analysis component") may also include website server 314, Vector Analysis Application 316, Event/Vector Mapping Application 318, Treatment/Recommendation Engine 320, and/or Report Generator 321.

In various implementations, applications 312 are stored in Memory 326 and operable on one or more Processors 302 to receive patient billing data from a multitude of care providers worldwide; map the patient billing data to an anonymous patient database, the patient billing data including billing codes and de-identified patient data; transform the billing codes and the patient data into multidimensional vectors; and analyze the multidimensional vectors to correlate diagnoses, treatment regimens, and treatment results with ailments of human anatomy, physiology, and psychology. In an embodiment, Medical Expert Server 112 includes a network communication component 330 coupled to the processor and adapted to return a real-time, network-based, collaborative patient treatment guide to a user interface of at least a subset of the multitude of care providers, based on a continuous real-time receipt of patient billing data, transformation of the billing data, and analysis of the multidimensional vectors.

In an embodiment, an analysis component of applications 312 is adapted to access an entry of patient billing data having multiple data fields; map each of the data fields to an integer value; and form a multidimensional vector representing the entry of billing data using each integer value of each data field of the entry of billing data to provide a magnitude component and a direction component to the multidimensional vector. In an example, the integer value of a data field is determined based on a diagnostic code or a patient code of the data field.

In another embodiment, an analysis component of applications 312 is adapted to form a super-vector from two or more multidimensional vectors, the super-vector having magnitude and direction components based on the two or more multidimensional vectors. The analysis component is adapted to analyze multiple super-vectors and to correlate diagnoses, treatment regimens, and treatment results with ailments of human anatomy, physiology, and psychology; and to return the real-time, network-based, collaborative patient treatment guide to at least a subset of the multitude of care providers, based on the correlation, as described herein.

Vector Analysis Application 316 may be configured to perform vector analysis and comparison of vectors and super vectors for patient identification, symptom and outcome mapping, tracking and correlation as described herein, and may be hosted on Medical Server Computer 112, or the like. In at least one of the various embodiments, Vector Analysis Application 316 may be operative on Medical Server Computer 112 of FIG. 1. In any event, Vector Analysis Application 316 may employ processes, or parts of processes, similar to those described in conjunction with FIGS. 5-8, to perform at least some of its actions.

Event/Vector Mapping Application 318 may be arranged and configured perform mapping, including vector and super vector mapping as described herein. In at least one of the various embodiments, Event/Vector Mapping Application 318 may be operative on Medical Server Computer 112 of FIG. 1. In any event, Event/Vector Mapping Application 318 may employ processes, or parts of processes, similar to those described in conjunction with FIGS. 5-8, to perform at least some of its actions.

Treatment/Recommendation Engine 320 may be arranged and configured to provide patent treatment recommendations as described herein. In at least one of the various embodiments, Treatment/Recommendation Engine 320 may be operative on Medical Server Computer 112 of FIG. 1. In any event, Treatment/Recommendation Engine 320 may employ processes, or parts of processes, similar to those described in conjunction with FIGS. 5-8, to perform at least some of its actions.

Report Generator 321 may be arranged and configured to determine and/or generate reports based on the vector analysis and care provider search and interaction. In at least one of the various embodiments, Report Generator 321 may be operative on Medical Expert System 112 of FIG. 1. In any event, Report Generator 321 may employ processes, or parts of processes, similar to those described in conjunction with FIGS. 5-8, to perform at least some of its actions.

In at least one of the various embodiments, the system can be configured to include Applications 312 for a Medical Trading System, which can be configured to provide training, volunteer, supply trading, and staffing solutions for care providers. In an embodiment, a trading application one or more trading algorithms (not shown) can be configured for equitable trading.

In at least one of the various embodiments, Applications 312 may include processes and/or API's for generating user interfaces.

In at least one of the various embodiments, Care Provider Server 114, or a separate Medical Trading System Server can be configured to interface with Medical Expert Server 112 to send and receive data, for example via a GUIs as descried herein.

Illustrative Logical System Architecture

Figure 4:
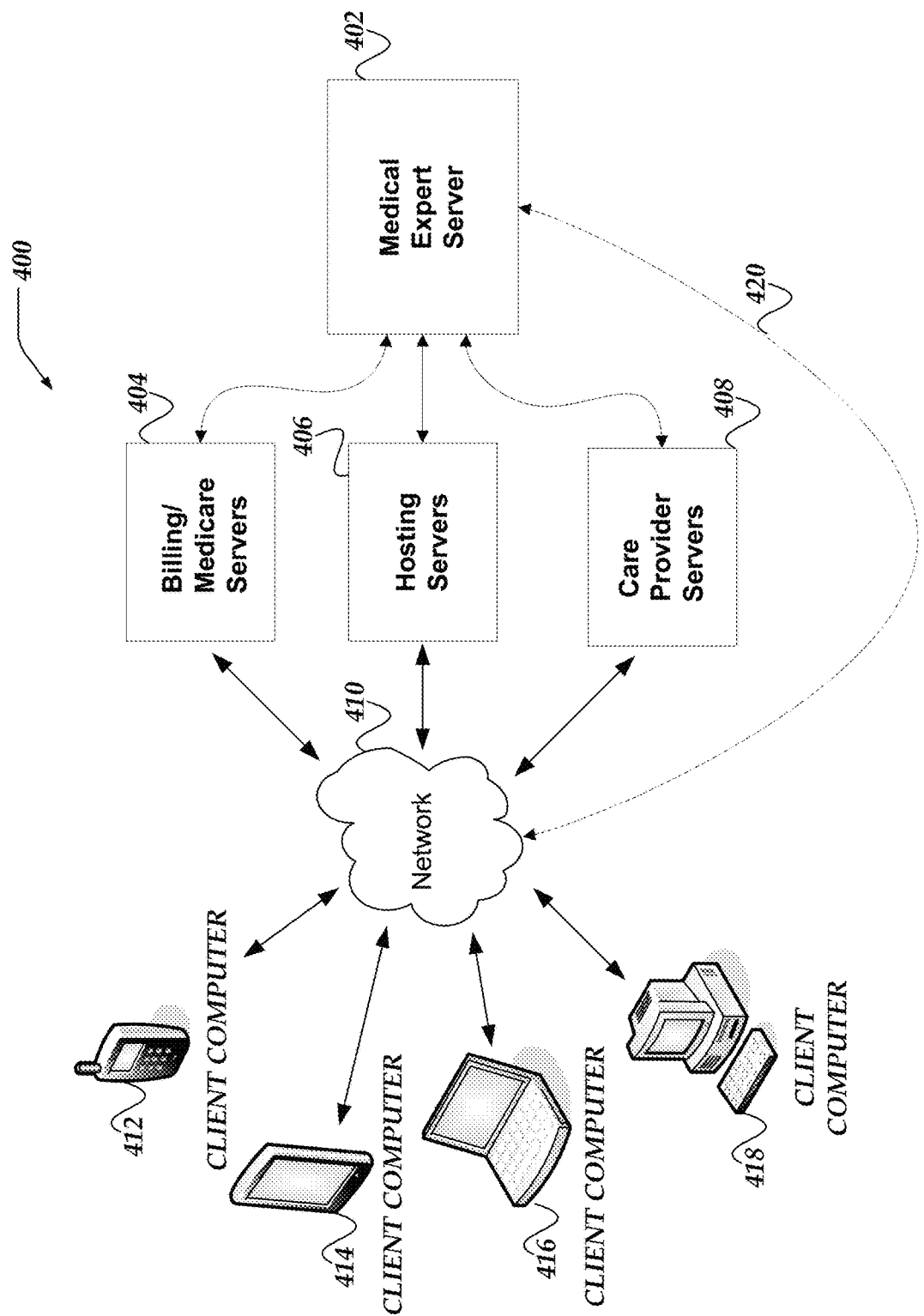
FIG. 4 illustrates a logical architecture of a healthcare system in accordance with at least one of the various embodiments.

FIG. 4 illustrates a logical architecture of system 400 for system for providing medical and patient data processing and treatment in accordance with at least one of the various embodiments. In at least one of the various embodiments, Medical Expert Server 402 may be arranged to be in communication with Billing Data Servers 404 (e.g. Medicare), Hosting Servers 406, Care Provider Services 408, or the like.

In at least one of the various embodiments, Medical Expert Server 402 may be one or more computers arranged to accept, store, and process de-identified patient vector and super vector data such as, Medical Expert Sever 112, or the like. In at least one of the various embodiments, Medical Expert Servers 402 may include one or more computers, such as, Medical Expert Server Computer 112, or the like. In at least one of the various embodiments, Medical Expert Server Computer 112 can include a Medical Trading Server.

In at least one of the various embodiments, Hosting Servers 406, may include one or more computers, such as, network computer 300, or the like, that host one or more types of content that are provided for care provider users. For example, hosting servers 406 may include one or more web servers providing web sites, third party provider care support, hosting sites, a Medical Trading System or the like. In at least one of the various embodiments, hosting servers may be arranged to integrate with Medical Expert Server 402.

In at least one of the various embodiments, Care Provider Servers 408, may include one or more care provider services, for example a hospital server, a Medical Trading System Sever or third party medical expert services. In at least one of the various embodiments, Medical Expert Server 402 may be arranged to integrate and/or communicate with Care Provider Services 408 using API's or other communication interfaces provided by the services. For example, one content provider service may offer a HTTP/REST based interface that enables Medical Expert Server 402 to determine various events that may be associated with treatment information provided by the service.

In at least one of the various embodiments, data and interfaces served from and/or hosted on Medical Expert Servers 404, Hosting Servers 406, Care Provider Servers 408 may be provided over network 410 to one or more client computers, such as, Client Computer 412, Client Computer 414, Client Computer 416, Client Computer 418, or the like.

In at least one of the various embodiments, communication between Medical Expert Servers 402 and Billing Data Servers 404, Hosting Servers 406, Care Provider Servers 408 may include one more events that may correspond to one or more actions and/or views. Further, Medical Expert Server 402 may be arranged to communicate directly or indirectly over network 410 to the Client Computers 412, 414, 416, 418 using one or more direct network paths, such as network path 420, for example for Client Computers of care providers. This communication may include information associated with one or more events occurring on the client computers.

In at least one of the various embodiments, Medical Expert Servers 402 may employ the communications from Billing Servers 404, Hosting Servers 406, Care Provider Servers 408, network path 420, or the like, to determine action information and/or view information corresponding to patient treatment data.

One of ordinary skill in the art will appreciate that the architecture of system 400 is a non-limiting example that is illustrative of at least a portion of at least one of the various embodiments. As such, more or less components may be employed and/or arranged differently without departing from the scope of the innovations described herein. However, system 400 is sufficient for disclosing at least the innovations claimed herein.

Figure 5A:
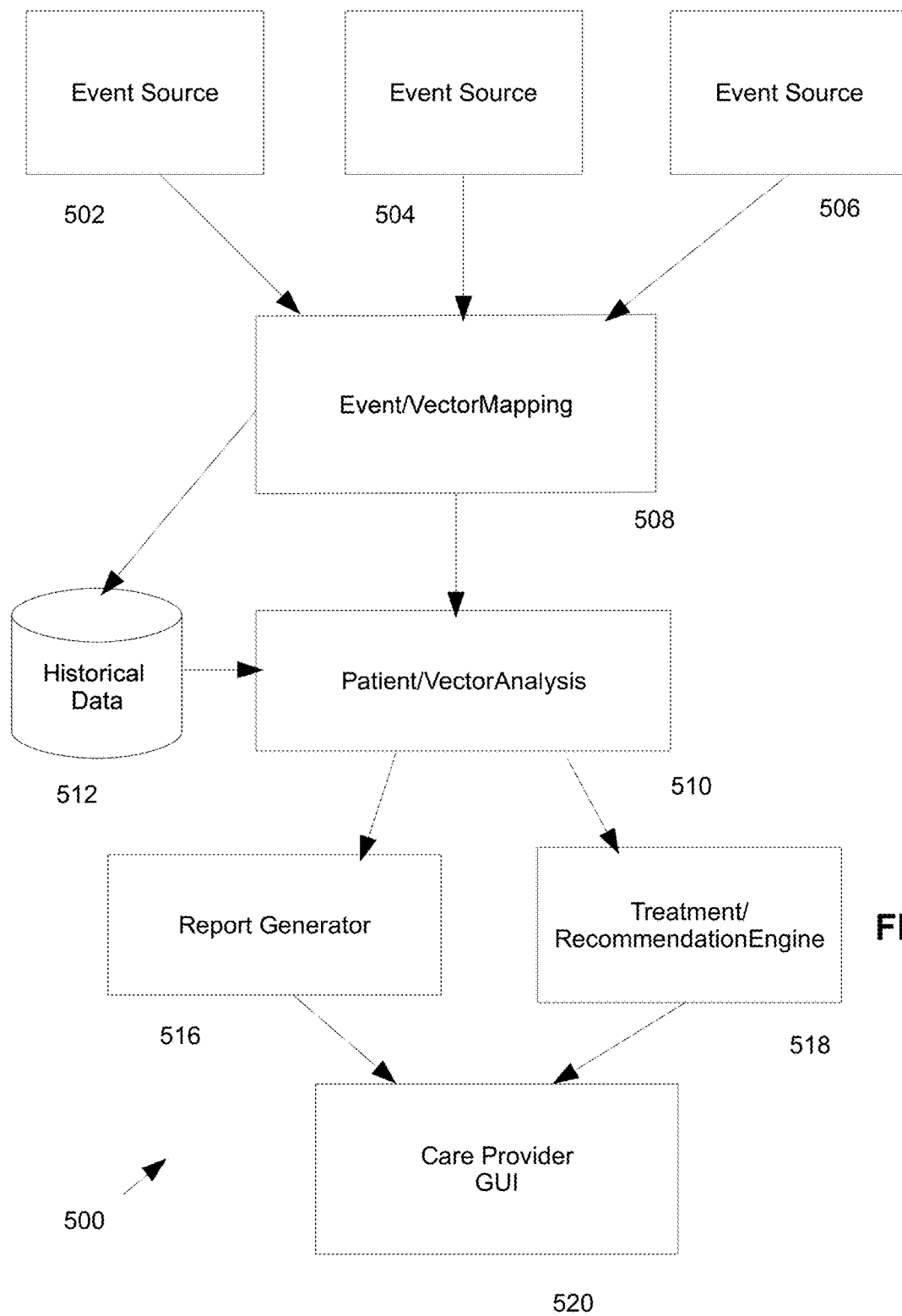

FIG. 5A represents a logical architecture for system 500 for multi-source vector data and exposure for analytics in accordance with at least one of the various embodiments. In at least one of the various embodiments, events from one or more event sources, such as, event source 502, event source 504, or event source 506 may be determined. In at least one of the various embodiments, event sources may include any source providing patent visit data and vector component data, such as Provider Servers 408, Hosting Servers 406, Billing Servers 404, Client Computer 412, Client Computer 414, Client Computer 416, Client Computer 418, network path 420, or the like. In at least one of the various embodiments, the determined events may correspond to various user interactions, display operations, or the like, related to vector coding and ailment searching data components, such as, Provider Servers 408, Hosting Servers 406, Billing Servers 404, Client Computer 412, Client Computer 414, Client Computer 416, Client Computer 418, network path 420 or the like. In at least one of the various embodiments, system 500 may any number event sources 502, 504, 506.

In at least one of the various embodiments, events that may be received and/or determined from one or more event sources, for example vector population from care providers as described herein, may be processed in vector/event mapping component 508. In at least one of the various embodiments, the various event sources may provide event information using a variety of data formats and/or communication protocols. Thus, event/vector mapping component 508 can be arranged to map to determined events into one or more actions and/or views. In at least one of the various embodiments, this mapping may normalize events that can be received from disparate event sources.

In at least one of the various embodiments, event/vector mapping component 508 may be arranged to use one or more filters, tests, rules, regular expressions, pattern matches, lookup tables, heuristics, or the like, for mapping the determined events to actions and/or views. In some embodiments, event mapping component 508 may be arranged to determine the particular, filters, tests, rules, regular expressions, pattern matches, lookup tables, heuristics, or the like, for mapping events based on the event source. For example, Medical Expert Server 112 computer may be configured to employ a particular set of filters and rules for mapping events from a particular care provider source.

In at least one of the various embodiments, event/vector mapping component 508 may generate one or more actions and/or views based on the determined events. In at least one of the various embodiments, information corresponding to each action and/or view may be stored using well-known data structures such as objects, hashes, arrays, linked lists, or the like. In at least one of the various embodiments, the action information and/or the event information may be stored in a database and associated with at least the care provider that corresponds to the data that is associated with the determined events.

In at least one of the various embodiments, the system is configured to employ programmable vector structures using, inter alia, billing codes, provider ID and time of medical visit as described herein. Vectors are programmable data structures (e.g., a Vector Class structure in Java).

In various embodiments, vectors can be created for billing codes, for example, for ICD codes and CPT codes. As of the present disclosure there are 13K ICD-9 Diagnosis Codes and 3 K ICD 9 Procedural Codes, 68K ICD-10 Diagnosis Codes and 87 K ICD-10 Procedural Codes, and 9,641 CPT Codes. One CPT code aligns and is justified by 4 ICD codes. In practice, the ICD codes are utilized to justify the utilization of a specific treatment, which is billed for a patient via the CPT code. The codes work in conjunction and are approved or rejected by Medicaid and other insurance companies. In various embodiments, billing codes can be mapped to ailments, anatomic and physiologic locations on the body along with the procedures performed by a care provider (e.g., doctor, medical professional). As described herein, in various embodiments, the billing codes are made actionable by transforming them into vectors. The vectors enable the historical data from billing coded visits (e.g.: ICD 9 & CPT billing codes) to be linked to current medical visits, enabling the doctors to pull up similar cases and gather treatment solutions for their patients in real time. In other words, the vector mapping unlocks the hidden data inside the medical codes. At least four major applications may make use of the disclosed techniques: (1) Automatically calculating quality measures (2) helping to stop medical fraud (3) Medical Research Applications and (4) Global Medical Portal—Medical Trading System.

In various implementations, as discussed herein, the techniques disclosed include transforming the medical billing codes, CPT/HCPCS, ICD 9 & 10, along with the pharmaceutical NDC drug codes. The each patient has a medical journey, which is captured by the billing codes submitted by their health care providers to the insurance companies in order to be compensated for their payments. The disclosed system transforms these codes into vectors (also arrays, matrices, and the like may be used), which are mathematical and computer data structures that facilitate the complex analysis of these codes. Currently code analysis is limited to counts and simple statistics such as mean, mode, frequently etc. With the disclosed system, vectors will facilitate the use of complex algorithms for billing code analytics.

In an implementation, the vectors are enhanced with META Data, which facilitates A Fully Customizable Medical Data Index. The META Data which populates the vectors will contain both textual and numerical information. The information on the following table (Table i) is for the ICD 10 Code for example.

TABLE i

| META Data | ICD 10 Code Code Name | I11.9 heart failure | E11.321 DM2 with mild nonproliferative retinopathy & macular edema |
|---|---|---|---|
| Side | | Unspecified by code | Unspecified by code |
| Problem Type | | High flood Pressure | Metabolic Syndrome |
| Problem Class | | Cardiovascular | Metabolic Disorder |
| Mortality Factor | | 15 | 25 |
| Morbidity Type | | | |
| Morbidity Scale | | 30 | 23 |
| Focused Anatomy | | Myocardium | Macula |
| Local Anatomy | | Ventricle | Retina |
| Broad Anatomy | | Cardiac | Eye |
| Global Anatomy-Physiology | | Cardiovscular | Visual Organ |
| Global System 1 | | Circulatory | Endocrine |
| Local System 1 | | Blood Pressure | Gluose Metabolism |
| System Problem | | High Blood Pressure | Hyperglycemia |
| Local System 2 | | Circulatory | Sensory System |
| Local System 2 | | Cardiac | Visual System |
| Initial Diagnosis Complication 1 | | None | None |
| Initial Diagnosis Complication 2 | | | |
| Initial Diagnosis Complication 3 | | | |
| Chronic Complication 1 | | None | Mild nonprolif retinopathy |
| Chronic Complication 2 | | | Macular edema |
| Chronic Complication 3 | | | |
| Visit Type | | Unspecified by code | Unspecified by code |

In various embodiments, a vector can be created for a Provider. A Provider ID is an alphanumeric number, which identifies a care provider's office location and specialty. This data does not raise privacy concerns, because it is not personally identifiable information and is obfuscated by the alphanumeric ID. The data, which can be used to populate vectors, is stored and accessible via the web in databases at the Centers for Medicare & Medicaid Services (CMS) <www.cms.gov>.

FIG. 5B shows an embodiment of a Provider Vector data structure. The Provider Vector can be expanded to include all the information that is attached to a Provider identification number, including 10 dimensions or vector components for: Provider ID, Specialty, Subspecialty (Subspecialty 1), Additional Subspecialty (Subspecialty 2), Provider Country, Provider State/Province, Provider City, Provider Geographical Sublocation (i.e., borough), Provider Geographical Sublocation 2, and Postal Code.

FIG. 5C shows an embodiment of a Time Vector data structure. The Time Vector is configured to hold information that is attached to the time in which the patient received a medical service, including 6 dimensions: Year, Month, Day, Hour, Minute, and Time Zone.

FIGS. 5D-5F shows embodiments of Billing Code Vector data structures. The Billing Code Vector Data Structures are configured to hold code data as well as diagnostic data correlated with the billing code data.

FIGS. 5D-5E show examples of a Billing Code Vector for an ICD Vector. The ICD-9 Billing Code Vector includes ICD-9 billing code data as well as components for data regarding clinically relevant related conditions and medical impact. The added vector data thereby codes a diagnosis into a broader description of personal and public health status. Historical CMS data can also be mapped. For example, the ICD-9 Billing Code Vector codes 7 dimensions of data: including added dimensions for Ailment Class, Physiologic Impact, and Pandemic Status in addition to ICD-9 dimensions for Diagnosis, Anatomic Location, Physiologic Location. As shown in FIGS. 5D-5E, raw data is mapped to integer data, as described in more detail herein. The vector is configured with added dimensions of Ailment Class, Physiologic Impact, and Pandemic Status to provide technologically more robust databases and algorithms for de-identified patient tracking and linking diagnostic and treatment information to historical and present billing code information.

FIG. 5F shows an example of a CPT Billing Code Vector. The CPT Vector comprises 10 dimensions: Procedure code, Procedure type/name, Procedure type 1 (invasiveness or non-invasive), Non Invasive Procedure type, Surgical Procedure Type 1 (technique), Surgical Procedure Type 2 (Invasiveness), Surgical Procedure Type 3 (Physiologic Impact), Anatomic Location, Physiologic System 1, and Physiologic System 2. Like the ICD-9 Vector, the CPT Vector is expanded to add dimensions for clinically relevant descriptions of the procedure type, invasiveness and physiologic impact to the CPT code data components, again providing a coding structure resulting in a technologically robust database for optimal algorithms for an medical expert system.

As noted above, as shown in FIGS. 5D-5E, raw data is mapped to integer data. The raw data for each of the dimensions/sub-dimensions, or components of each vector can mapped to integers (e.g, Provider ID 1-9999999, Physician Specialty mapped to integers 1-100, Physician Subspecialty mapped to integers 1-100, Date of Service mapped to integers based on programming language, etc.). Integer mapping of each of the vector components allows for normalization and correlation of the data as shown below.

As will be appreciated, data can be provided from sources employing other billing code systems or formats for identification (e.g. from other jurisdictions, entities, agencies charged with managing billing information), and vectors can be configured accordingly.

In various embodiments the system is configured to compile the Provider Vector, Time Vector, Billing Code Vectors (e.g. ICD and CPT Vectors) into a single vector representing a patient's visit to a care provider, described herein as a "super vector." As described herein, each time a patient visits a care provider, the provider can select the physical system and ailment he or she is dealing with. The system can then employ the vectors as described herein to map data for a patient's visit with a care provider to historical vector data correlated with the medical billing codes. Historical vector data can be derived from prior care provider visits entered by the care provider or derived from databases warehousing such data, such as billing databases (e.g., databases at the Centers for Medicare & Medicaid Services (CMS)<www.cms.gov>). Based on information returned via the vector mapping, the care provider can make a treatment decision.

A super vector can include a Provider Vector, a Time vector, and one or more Billing Code Vectors. An exemplary super vector is given in Table 1.

TABLE 1

| Dimension | Sub Vector | Sub Dimension | Data |
|---|---|---|---|
| 1 | Provider Data Vector | 1 | Provider ID |
| 2 | | 2 | Specialty |
| 3 | | 3 | Sub Specialty 1 |
| 4 | | 4 | Sub Specialty 2 |
| 5 | | 5 | Country |
| 6 | | 6 | State/Province |
| 7 | | 7 | City |
| 8 | | 8 | Geo Sub 1 |
| 9 | | 9 | Geo Sub 2 |
| 10 | | 10 | Postal Code |
| 11 | Time Vector | 1 | Year |
| 12 | | 2 | Month |
| 13 | | 3 | Day |
| 14 | | 4 | Hour |
| 15 | | 5 | Minute |
| 16 | | 6 | Time Zone |
| 17 | ICD Data Vector 1 | 1 | Code |
| 18 | | 2 | Diagnosis |
| 19 | | 3 | Ailment |
| 20 | | 4 | Anatomic Location |
| 21 | | 5 | Physiologic System |
| 22 | | 6 | Impact |
| 23 | | 7 | Pandemic |
| 24 | ICD Data Vector 2 | 1 | Code |
| 25 | | 2 | Diagnosis |
| 26 | | 3 | Ailment |
| 27 | | 4 | Anatomic Location |
| 28 | | 5 | Physiologic System |
| 29 | | 6 | Impact |
| 30 | | 7 | Pandemic |
| 31 | ICD Data Vector 3 | 1 | Code |
| 32 | | 2 | Diagnosis |
| 33 | | 3 | Ailment |
| 34 | | 4 | Anatomic Location |
| 35 | | 5 | Physiologic System |
| 36 | | 6 | Impact |
| 37 | | 7 | Pandemic |
| 38 | ICD Data Vector 4 | 1 | Code |
| 39 | | 2 | Diagnosis |
| 40 | | 3 | Ailment |
| 41 | | 4 | Anatomic Location |
| 42 | | 5 | Physiologic System |
| 43 | | 6 | Impact |
| 44 | | 7 | Pandemic |
| 45 | ICD Data Vector 5 | 1 | Code |
| 46 | | 2 | Diagnosis |
| 47 | | 3 | Ailment |
| 48 | | 4 | Anatomic Location |
| 49 | | 5 | Physiologic System |
| 50 | | 6 | Impact |
| 51 | | 7 | Pandemic |
| 52 | ICD Data Vector 6 | 1 | Code |
| 53 | | 2 | Diagnosis |
| 54 | | 3 | Ailment |
| 55 | | 4 | Anatomic Location |
| 56 | | 5 | Physiologic System |
| 57 | | 6 | Impact |
| 58 | | 7 | Pandemic |
| 59 | ICD Data Vector 7 | 1 | Code |
| 60 | | 2 | Diagnosis |
| 61 | | 3 | Ailment |
| 62 | | 4 | Anatomic Location |
| 63 | | 5 | Physiologic System |
| 64 | | 6 | Impact |
| 65 | | 7 | Pandemic |
| 66 | ICD Data Vector 8 | 1 | Code |
| 67 | | 2 | Diagnosis |
| 68 | | 3 | Ailment |
| 69 | | 4 | Anatomic Location |
| 70 | | 5 | Physiologic System |
| 71 | | 6 | Impact |
| 72 | | 7 | Pandemic |
| 73 | CPT Data Vector 1 | 1 | Code |
| 74 | | 2 | Procedure Type |
| 75 | | 3 | Procedure Type 1 (Invasiveness) |
| 76 | | 4 | Non Invasive Procedure Type |
| 77 | | 5 | Surgical Procedure Type 1 (Technique) |
| 78 | | 6 | Surgical Procedure Type 2 (Invasiveness) |
| 79 | | 7 | Surgical Procedure Type 1 (Impact) |
| 80 | | 8 | Anatomic Location |
| 81 | | 9 | Physiologic System 1 |
| 82 | | 10 | Physiologic System 2 |
| 83 | CPT Data Vector 2 | 1 | Code |
| 84 | | 2 | Procedure Type |
| 85 | | 3 | Procedure Type 1 (Invasiveness) |
| 86 | | 4 | Non Invasive Procedure Type |
| 87 | | 5 | Surgical Procedure Type 1 (Technique) |
| 88 | | 6 | Surgical Procedure Type 2 (Invasiveness) |
| 89 | | 7 | Surgical Procedure Type 1 (Impact) |
| 90 | | 8 | Anatomic Location |
| 91 | | 9 | Physiologic System 1 |
| 92 | | 10 | Physiologic System 2 |

As shown in Table 1, an exemplary super vector includes 12 sub vectors: a Provider Vector, a Time Vector and 10 Billing Vectors having 8 ICD Vectors and 2 CPT Vectors. The super vector includes 92 dimensions for the mapping vector data of a patient visit, with each sub vector including sub dimensions as described with respect to FIGS. 7A-7E.

In at least one of the various embodiments, a Patient/Vector analysis component 510 may be arranged to determine identify patients and treatment information based on vector information associated with a patient care and treatment system. Also, in at least one of the various embodiments, the analysis may include determining historical vector information from a record store, such as, historical data information database 512. In at least one of the various embodiments, historical information database 512 may include historical vector and super vector data as described herein. The historical data can also include action information, view information, performance information, or the like, previously associated with, inter alia, a care provider or patient or related services and entities. Thus, in at least one of the various embodiments, historical information database 512 is a storehouse of past treatment and vector information that is associated with care providers and patients.

As shown in Table 2, raw data for vector mapping maps a plurality of vectors as sub-vectors of a super vector for a given visit such that the system can identify the patient and past patient visits while preserving patient anonymity. The following exemplary super vector is shown including a Provider subvector, a Time subvector, and 6 Billing Vectors (4 ICD Vectors and 2 CPT Vectors). However as described above a super vector can have any number of vectors, including the 12 subvectors as described with respect to Table 1 or more. The super vector shows raw information for 6 cases, which can be translated to system hits, associated with the super vector dimensions.

TABLE 2

|  | Super vector | Case (Hit) | | | | | |
|---|---|---|---|---|---|---|---|
|  |  | 1 | 2 | *3* | 4 | 5 | *6* |
| Provider ID | Provider ID | 21345466 | 94560456 | *56964405* | 505433433 | 56444643 | *34567005* |
|  | Specialty | Int Med | Cardiology | *Int Med* | OB GYN | Ortho | *Int Med* |
|  | Sub Specialty 1 | None | None | *None* | None | Sports | *None* |
|  | Sub Specialty 2 |  |  |  |  |  |  |
|  | Country | USA | USA | *USA* | USA | USA | *USA* |
|  | State/Province | New York | New York | *New York* | New York | New York | *New York* |
|  | City | Westchester | Westchester | *Westchester* | Westchester | Westchester | *Westchester* |
|  | Geo Sub 1 | None | None | *None* | None | None | *None* |
|  | Geo Sub 2 | None | None | *None* | None | None | *None* |
|  | Postal Code | 10507 | 10505 | *10507* | 10506 | 10510 | *10507* |
| Time | Year | 2015 | 2015 | *2015* | 2005 | 2015 | *2015* |
|  | Month | March | March | *March* | March | March | *March* |
|  | Day | 1 | 4 | *1* | 4 | 3 | *10* |
|  | Hour | 9 | 9 | *9* | 9 | 9 | *9* |
|  | Minute | 5 | 15 | *20* | 30 | 45 | *55* |
|  | Time Zone | EST | EST | *EST* | EST | EST | *EST* |
| ICD 1 | Code | 401.9 | 401.9 | *401.9* | 626.2 | 726.1 | *401.9* |
|  | Diagnosis | Essential hypertension | Essential hypertension | *Essential hypertension* | Meno metrorrhagia | Subacromial bursitis | *Essential hypertension* |
|  | Ailment | Metabolic Syndrome | Metabolic Syndrome | *Metabolic Syndrome* | Dysmenorrhea | Rotator Cuff Syndrome | *Metabolic Syndrome* |
|  | Anatomic Location | Heart | Heart | *Heart* | Uterus | Shoulder | *Heart* |
|  | Physiologic System | Cardiovascular | Cardiovascular | *Cardiovascular* | Female Genitourinary | Musculoskeletal | *Cardiovascular* |
|  | Impact | Moderate | Moderate | *Moderate* | Severe | Moderate | *Moderate* |
|  | Pandemic | No | No | *No* | No | No | *No* |
| ICD 2 | Code | 272.0 | 272.0 | *272.0* | None | None | *272.0* |
|  | Diagnosis | Hyper-cholesterolemia | Hyper-cholesterolemia | *Hypercholesterolemia* | None | None | *Hypercholesterolemia* |
|  | Ailment | Metabolic Syndrome | Metabolic Syndrome | *Metabolic Syndrome* | None | None | *Metabolic Syndrome* |
|  | Anatomic Location | Liver | Liver | *Liver* | None | None | *Liver* |
|  | Physiologic System | Cardiovascular | Cardiovascular | *Cardiovascular* | None | None | *Cardiovascular* |
|  | Impact | Moderate | Moderate | *Moderate* | None | None | *Moderate* |
|  | Pandemic | No | No | *No* | No | No | *No* |
| ICD 3 | Code | 250.02 | 413.9 | *250.02* | None | None | *250.02* |
|  | Diagnosis | Diabetes Mellitus II, uncontrolled | Angina Pectoris | *Diabetes Mellitus II, uncontrolled* | None | None | *Diabetes Mellitus II, uncontrolled* |
|  | Ailment | Metabolic Syndrome | Cardiac Ischemia | *Metabolic Syndrome* | None | None | *Metabolic Syndrome* |
|  | Anatomic Location | Pancreas | Heart | *Pancreas* | None | None | *Pancreas* |
|  | Physiologic System | Endocrine | Cardiovascular | *Endocrine* | None | None | *Endocrine* |
|  | Impact | Severe | Severe | *Severe* | None | None | *Severe* |
|  | Pandemic | No | No | *No* | None | None | *No* |
| ICD 4 | Code | 250.6 | 427.31 | *250.6* | None | None | *250.6* |
|  | Diagnosis | Diabetic Neuropathy | Atrial fibrillation | *Diabetic Neuropathy* | None | None | *Diabetic Neuropathy* |
|  | Ailment | Neuropathy | Arrhythmia | *Neuropathy* | None | None | *Neuropathy* |
|  | Anatomic Location | Feet | Heart | *Feet* | None | None | *Feet* |
|  | Physiologic System | Neurologic | Cardiovascular | *Neurologic* | None | None | *Neurologic* |
|  | Impact | Severe | Severe | *Severe* | None | None | *Severe* |
|  | Pandemic | No | No | *No* | None | None | *No* |
| CPT 1 | Code | 99203 | 99203 | *99213* | 99204 | 99204 | *99213* |
|  | Procedure Type | New Patient E&M Level 3 | New Patient E&M Level 3 | *Established Patient Level 3* | New Patient E&M Level 4 | New Patient E&M Level 4 | *Established Patient Level 3* |
|  | Procedure Type 1 (Invasiveness) | Non Invasive | Non Invasive | *Non Invasive* | Non Invasive | Non Invasive | *Non Invasive* |

TABLE 2-continued

| | Super vector | 1 | 2 | 3 | 4 | 5 | 6 |
|---|---|---|---|---|---|---|---|
| | Non Invasive Procedure Type | E&M | E&M | *E&M* | E&M | E&M | *E&M* |
| | Surgical Procedure Type 1 (Technique) | None | None | *None* | None | None | *None* |
| | Surgical Procedure Type2 (Invasiveness) | None | None | *None* | None | None | *None* |
| | Surgical Procedure Type 1 (Impact) | None | None | *None* | None | None | *None* |
| | Anatomic Location | None | None | *None* | None | None | *None* |
| | Physiologic System | None | None | *None* | None | None | *None* |
| | Physiologic System | None | None | *None* | None | None | *None* |
| CPT 1 | Code | 71020 | None | *None* | None | 73030 | *None* |
| | Procedure Type | Chest Xray | None | *None* | None | Shoulder Xray | *None* |
| | Procedure Type 1 (Invasiveness) | Non Invasive | None | *None* | None | Non Invasive | *None* |
| | Non Invasive Procedure Type | Imaging | None | *None* | None | Imaging | *None* |
| | Surgical Procedure Type 1 (Technique) | None | None | *None* | None | None | *None* |
| | Surgical Procedure Type2 (Invasiveness) | None | None | *None* | None | None | *None* |
| | Surgical Procedure Type 1 (Impact) | None | None | *None* | None | None | *None* |
| | Anatomic Location | Thorax | None | *None* | None | Shoulder | *None* |
| | Physiologic System | Respiratory | None | *None* | None | Musculoskeletal | *None* |
| | Physiologic System | Cardiovascular | None | *None* | None | None | *None* |
| CPT 1 | Code | None | None | *None* | None | 20610 | *None* |
| | Procedure Type | None | None | *None* | None | Injection Major Joint | *None* |
| | Procedure Type 1 (Invasiveness) | None | None | *None* | None | Invasive | *None* |
| | Non Invasive Procedure Type | None | None | *None* | None | Injection | *None* |
| | Surgical Procedure Type 1 (Technique) | None | None | *None* | None | None | *None* |
| | Surgical Procedure Type2 (Invasiveness) | None | None | *None* | None | None | *None* |
| | Surgical Procedure Type 1 (Impact) | None | None | *None* | None | None | *None* |
| | Anatomic Location | None | None | *None* | None | Shoulder | *None* |
| | Physiologic System | None | None | *None* | None | Musculoskeletal | *None* |

TABLE 2-continued

|  |  | Case (Hit) | | | | | |
|---|---|---|---|---|---|---|---|
| Super vector | | 1 | 2 | *3* | 4 | 5 | *6* |
| CPT 1 | Physiologic System | None | None | *None* | None | None | *None* |
|  | Code | None | None | *None* | None | None | *None* |
|  | Procedure Type | None | None | *None* | None | None | *None* |
|  | Procedure Type 1 (Invasiveness) | None | None | *None* | None | None | *None* |
|  | Non Invasive Procedure Type | None | None | *None* | None | None | *None* |
|  | Surgical Procedure Type 1 (Technique) | None | None | *None* | None | None | *None* |
|  | Surgical Procedure Type2 (Invasiveness) | None | None | *None* | None | None | *None* |
|  | Surgical Procedure Type 1 (Impact) | None | None | *None* | None | None | *None* |
|  | Anatomic Location | None | None | *None* | None | None | *None* |
|  | Physiologic System 1 | None | None | *None* | None | None | *None* |
|  | Physiologic System 2 | None | None | *None* | None | None | *None* |
| Provider ID | Provider ID | 21345466 | 94560456 | *56964405* | 505433433 | 56444643 | *34567005* |
|  | Specialty | Int Med | Cardiology | *Int Med* | OB GYN | Ortho | *Int Med* |
|  | Sub Specialty 1 | None | None | *None* | None | Sports | *None* |
|  | Sub Specialty 2 |  |  |  |  |  |  |
|  | Country | USA | USA | *USA* | USA | USA | *USA* |
|  | State/Province | New York | New York | *New York* | New York | New York | *New York* |
|  | City | Westchester | Westchester | *Westchester* | Westchester | Westchester | *Westchester* |
|  | Geo Sub 1 | None | None | *None* | None | None | *None* |
|  | Geo Sub 2 | None | None | *None* | None | None | *None* |
|  | Postal Code | 10505 | 10505 | *10507* | 10506 | 10510 | *10507* |
|  | Year | 2015 | 2015 | *2015* | 2005 | 2015 | *2015* |
|  | Month | March | March | *March* | March | March | *March* |
|  | Time Day | 1 | 4 | *1* | 4 | 3 | *10* |
|  | Hour | 9 | 9 | *9* | 9 | 9 | *9* |
|  | Minute | 5 | 15 | *20* | 30 | 45 | *55* |
|  | Time Zone | EST | EST | *EST* | EST | EST | *EST* |
| ICD 1 | Code | 401.9 | 401.9 | *401.9* | 626.2 | 726.1 | *401.9* |
|  | Diagnosis | Essential hypertension | Essential hypertension | *Essential hypertension* | Meno- metrorrhagia | Subacromial bursitis | *Essential hypertension* |
|  | Ailment | Metabolic Syndrome | Metabolic Syndrome | *Metabolic Syndrome* | Dys menorrhea | Rotator Cuff Syndrome | *Metabolic Syndrome* |
|  | Anatomic Location | Heart | Heart | *Heart* | Uterus | Shoulder | *Heart* |
|  | Physiologic System | Cardiovascular | Cardiovascular | *Cardiovascular* | Female Genitourinary | Musculoskeletal | *Cardiovascular* |
|  | Impact | Moderate | Moderate | *Moderate* | Severe | Moderate | *Moderate* |
|  | Pandemic | No | No | *No* | No | No | *No* |
| ICD 2 | Code | 272.0 | 272.0 | *272.0* | None | None | *272.0* |
|  | Diagnosis | Hyper- cholesterolemia | Hyper- cholesterolemia | *Hypercholesterolemia* | None | None | *Hypercholesterolemia* |
|  | Ailment | Metabolic Syndrome | Metabolic Syndrome | *Metabolic Syndrome* | None | None | *Metabolic Syndrome* |
|  | Anatomic Location | Liver | Liver | *Liver* | None | None | *Liver* |
|  | Physiologic System | Cardiovascular | Cardiovascular | *Cardiovascular* | None | None | *Cardiovascular* |
|  | Impact | Moderate | Moderate | *Moderate* | None | None | *Moderate* |
|  | Pandemic | No | No | *No* | None | None | *No* |
| ICD 3 | Code | 250.02 | 413.9 | *250.02* | None | None | *250.02* |
|  | Diagnosis | Diabetes Mellitus II, uncontrolled | Angina Pectoris | *Diabetes Mellitus II, uncontrolled* | None | None | *Diabetes Mellitus II, uncontrolled* |
|  | Ailment | Metabolic Syndrome | Cardiac Ischemia | *Metabolic Syndrome* | None | None | *Metabolic Syndrome* |

TABLE 2-continued

|  | Super vector | Case (Hit) | | | | | |
|---|---|---|---|---|---|---|---|
|  |  | 1 | 2 | *3* | 4 | 5 | *6* |
|  | Anatomic Location | Pancreas | Heart | *Pancreas* | None | None | *Pancreas* |
|  | Physiologic System | Endocrine | Cardiovascular | *Endocrine* | None | None | *Endocrine* |
|  | Impact | Severe | Severe | *Severe* | None | None | *Severe* |
|  | Pandemic | No | No | *No* | None | None | *No* |
| ICD 4 | Code | 250.6 | 427.31 | *250.6* | None | None | *250.6* |
|  | Diagnosis | Diabetic Neuropathy | Atrial fibrillation | *Diabetic Neuropathy* | None | None | *Diabetic Neuropathy* |
|  | Ailment | Neuropathy | Arrhymthia | *Neuropathy* | None | None | *Neuropathy* |
|  | Anatomic Location | Feet | Heart | *Feet* | None | None | *Feet* |
|  | Physiologic System | Neurologic | Cardiovascular | *Neurologic* | None | None | *Neurologic* |
|  | Impact | Severe | Severe | *Severe* | None | None | *Severe* |
|  | Pandemic | No | No | *No* | None | None | *No* |
| CPT 1 | Code | 99203 | 99203 | *99213* | 99204 | 99204 | *99213* |
|  | Procedure Type | New Patient E&M Level 3 | New Patient E&M Level 3 | *Established Patient Level 3* | New Patient E&M Level 4 | New Patient E&M Level 4 | *Established Patient Level 3* |
|  | Procedure Type 1 (Invasiveness) | Non Invasive | Non Invasive | *Non Invasive* | Non Invasive | Non Invasive | *Non Invasive* |
|  | Non Invasive Procedure Type | E&M | E&M | *E&M* | E&M | E&M | *E&M* |
|  | Surgical Procedure Type 1 (Technique) | None | None | *None* | None | None | *None* |
|  | Surgical Procedure Type 2 (Invasiveness) | None | None | *None* | None | None | *None* |
|  | Surgical Procedure Type 1 (Impact) | None | None | *None* | None | None | *None* |
|  | Anatomic Location | None | None | *None* | None | None | *None* |
|  | Physiologic System | None | None | *None* | None | None | *None* |
|  | Physiologic System | None | None | *None* | None | None | *None* |
| CPT 1 | Code | 71020 | None | *None* | None | 73030 | *None* |
|  | Procedure Type | Chest Xray | None | *None* | None | Shoulder Xray | *None* |
|  | Procedure Type 1 (Invasiveness) | Non Invasive | None | *None* | None | Non Invasive | *None* |
|  | Non Invasive Procedure Type | Imaging | None | *None* | None | Imaging | *None* |
|  | Surgical Procedure Type 1 (Technique) | None | None | *None* | None | None | *None* |
|  | Surgical Procedure Type 2 (Invasiveness) | None | None | *None* | None | None | *None* |
|  | Surgical Procedure Type 1 (Impact) | None | None | *None* | None | None | *None* |
|  | Anatomic Location | Thorax | None | *None* | None | Shoulder | *None* |
|  | Physiologic System | Respiratory | None | *None* | None | Musculoskeletal | *None* |
|  | Physiologic System | Cardiovascular | None | *None* | None | None | *None* |
| CPT 1 | Code | None | None | *None* | None | 20610 | *None* |
|  | Procedure Type | None | None | *None* | None | Injection Major Joint | *None* |

TABLE 2-continued

|  |  | Case (Hit) | | | | | |
|---|---|---|---|---|---|---|---|
| Super vector | | 1 | 2 | *3* | 4 | 5 | *6* |
| | Procedure Type 1 (Invasiveness) | None | None | *None* | None | Invasive | *None* |
| | Non Invasive Procedure Type | None | None | *None* | None | Injection | *None* |
| | Surgical Procedure Type 1 (Technique) | None | None | *None* | None | None | *None* |
| | Surgical Procedure Type 2 (Invasiveness) | None | None | *None* | None | None | *None* |
| | Surgical Procedure Type 1 (Impact) | None | None | *None* | None | None | *None* |
| | Anatomic Location | None | None | *None* | None | Shoulder | *None* |
| | Physiologic System | None | None | *None* | None | Musculoskeletal | *None* |
| | Physiologic System | None | None | *None* | None | None | *None* |
| CPT 1 | Code | None | None | *None* | None | None | *None* |
| | Procedure Type | None | None | *None* | None | None | *None* |
| | Procedure Type 1 (Invasiveness) | None | None | *None* | None | None | *None* |
| | Non Invasive Procedure Type | None | None | *None* | None | None | *None* |
| | Surgical Procedure Type 1 (Technique) | None | None | *None* | None | None | *None* |
| | Surgical Procedure Type 2 (Invasiveness) | None | None | *None* | None | None | *None* |
| | Surgical Procedure Type 1 (Impact) | None | None | *None* | None | None | *None* |
| | Anatomic Location | None | None | *None* | None | None | *None* |
| | Physiologic System 1 | None | None | *None* | None | None | *None* |
| | Physiologic System 2 | None | None | *None* | None | None | *None* |

As shown in Table 2, the system is configured to populate super vectors with raw data that can be employed to identify matches. For example, the system can determine based on matching dimensional data of the super vectors that cases 3 and 6 (bold italics) are the same patient based on the matched dimensions. In an embodiment, the system is configured to map the data by mapping the dimensional data for the super vector into integers, as shown in Table 3.

TABLE 3

| | Existing Virtual Patient (1-5) | | | | | New Entry/ Case/Hit (6) |
|---|---|---|---|---|---|---|
| Mapped Data | 1 | 2 | 3 | 4 | 5 | 6 |
| Provider ID | 21345466 | 94560456 | 56964405 | 505433433 | 56444643 | 34567005 |
| | 10000 | 20000 | 10000 | 30000 | 40000 | 10000 |
| | 10000 | 10000 | 10000 | 10000 | 20000 | 10000 |
| | 42064 | 42067 | 42064 | 42067 | 42066 | 42073 |
| | 10000 | 10000 | 10000 | 10000 | 10000 | 10000 |

TABLE 3-continued

| | Existing Virtual Patient (1-5) | | | | | New Entry/Case/Hit (6) |
|---|---|---|---|---|---|---|
| Mapped Data | 1 | 2 | 3 | 4 | 5 | 6 |
| | 10000 | 10000 | 10000 | 10000 | 10000 | 10000 |
| | 10000 | 10000 | 10000 | 10000 | 10000 | 10000 |
| | 0 | 0 | 0 | 0 | 0 | 0 |
| | 0 | 0 | 0 | 0 | 0 | 0 |
| | 10507 | 10505 | 10507 | 10506 | 10510 | 10507 |
| Time | 2015 | 2015 | 2015 | 2005 | 2015 | 2015 |
| | 3 | 3 | 3 | 3 | 3 | 3 |
| | 1 | 4 | 1 | 4 | 3 | 10 |
| | 9 | 9 | 9 | 9 | 9 | 9 |
| | 5 | 15 | 20 | 30 | 45 | 55 |
| | 1 | 1 | 1 | 1 | 1 | 1 |
| ICD 1 | 10000 | 10000 | 10000 | 70000 | 80000 | 10000 |
| | 10000 | 10000 | 10000 | 20000 | 30000 | 10000 |
| | 10000 | 10000 | 10000 | 20000 | 30000 | 10000 |
| | 10000 | 10000 | 10000 | 20000 | 30000 | 10000 |
| | 2.0 | 2.0 | 2.0 | 3.0 | 2.0 | 2.0 |
| | 0.0 | 0.0 | 0.0 | 0.0 | 0.0 | 0.0 |
| ICD 2 | 20000 | 20000 | 20000 | 1000 | 1000 | 20000 |
| | 10000 | 10000 | 10000 | 1000 | 1000 | 10000 |
| | 40000 | 40000 | 40000 | 1000 | 1000 | 40000 |
| | 10000 | 10000 | 10000 | 1000 | 1000 | 10000 |
| | 2 | 2 | 2 | 1000 | 1000 | 2 |
| | 0 | 0 | 0 | 1000 | 1000 | 0 |
| ICD 3 | 30000 | 50000 | 30000 | 1000 | 1000 | 30000 |
| | 10000 | 40000 | 10000 | 1000 | 1000 | 10000 |
| | 50000 | 10000 | 50000 | 1000 | 1000 | 50000 |
| | 40000 | 10000 | 40000 | 1000 | 1000 | 40000 |
| | 3 | 3 | 3 | 1000 | 1000 | 3 |
| | 0 | 0 | 0 | 1000 | 1000 | 0 |
| ICD 4 | 40000 | 90000 | 40000 | 1000 | 1000 | 40000 |
| | 60000 | 50000 | 60000 | 1000 | 1000 | 60000 |
| | 70000 | 10000 | 70000 | 1000 | 1000 | 70000 |
| | 50000 | 10000 | 50000 | 1000 | 1000 | 50000 |
| | 3 | 3 | 3 | 1000 | 1000 | 3 |
| | 0 | 0 | 0 | 1000 | 1000 | 0 |
| | 99203 | 99203 | 99213 | 99204 | 99204 | 99213 |
| CPT 1 | 0 | 0 | 0 | 0 | 0 | 0 |
| | 10000 | 10000 | 10000 | 10000 | 10000 | 10000 |
| | 1000 | 1000 | 1000 | 1000 | 1000 | 1000 |
| | 1000 | 1000 | 1000 | 1000 | 1000 | 1000 |
| | 1000 | 1000 | 1000 | 1000 | 1000 | 1000 |
| | 1000 | 1000 | 1000 | 1000 | 1000 | 1000 |
| | 1000 | 1000 | 1000 | 1000 | 1000 | 1000 |
| | 1000 | 1000 | 1000 | 1000 | 1000 | 1000 |
| | 71020 | 1000 | 1000 | 1000 | 73030 | 1000 |
| CPT 1 | 0 | 1000 | 1000 | 1000 | 0 | 1000 |
| | 20000 | 1000 | 1000 | 1000 | 20000 | 1000 |
| | 1000 | 1000 | 1000 | 1000 | 1000 | 1000 |
| | 1000 | 1000 | 1000 | 1000 | 1000 | 1000 |
| | 1000 | 1000 | 1000 | 1000 | 1000 | 1000 |
| | 80000 | 1000 | 1000 | 1000 | 30000 | 1000 |
| | 60000 | 1000 | 1000 | 1000 | 30000 | 1000 |
| | 10000 | 1000 | 1000 | 1000 | 1000 | 1000 |
| | 10000 | 10000 | 1000 | 1000 | 20610 | 1000 |
| CPT 1 | 10000 | 10000 | 1000 | 1000 | 1 | 1000 |
| | 10000 | 10000 | 1000 | 1000 | 10000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 30000 | 1000 |
| | 10000 | 10000 | 1000 | 1000 | 30000 | 1000 |
| | 10000 | 10000 | 1000 | 1000 | 1000 | 1000 |
| | 10000 | 10000 | 1000 | 1000 | 1000 | 1000 |

TABLE 3-continued

| | Existing Virtual Patient (1-5) | | | | | New Entry/Case/Hit (6) |
|---|---|---|---|---|---|---|
| Mapped Data | 1 | 2 | 3 | 4 | 5 | 6 |
| CPT 1 | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |
| | 10000 | 10000 | 1000 | 1000 | 1000 | 1000 |

The system is configured to normalize the integer vector data of Table 3 and produce the normalized data as shown in Table 4 so that correlation algorithms can be employed to identify patients from the historical super vector data with a high degree of probability as shown in Table 5.

TABLE 4

| 1 | 2 | 3 | 4 | 5 | 6 |
|---|---|---|---|---|---|
| 0.99994516 | 0.999998203 | 0.999994968 | 0.999999962 | 0.999994802 | 0.999986333 |
| 0.000468458 | 0.000211505 | 0.000175547 | 5.9355E−05 | 0.000708655 | 0.000289289 |
| 0.000468458 | 0.000105752 | 0.000175547 | 1.9785E−05 | 0.000354328 | 0.000289289 |
| 0.001970521 | 0.000444868 | 0.000738422 | 8.32296E−05 | 0.000745257 | 0.001217127 |
| 0.000468458 | 0.000105752 | 0.000175547 | 1.9785E−05 | 0.000177164 | 0.000289289 |
| 0.000468458 | 0.000105752 | 0.000175547 | 1.9785E−05 | 0.000177164 | 0.000289289 |
| 0.000468458 | 0.000105752 | 0.000175547 | 1.9785E−05 | 0.000177164 | 0.000289289 |
| 0 | 0 | 0 | 0 | 0 | 0 |
| 0 | 0 | 0 | 0 | 0 | 0 |
| 0.000492209 | 0.000111093 | 0.000184448 | 2.07861E−05 | 0.000186199 | 0.000303956 |
| 9.43943E−05 | 2.13091E−05 | 3.53728E−05 | 3.96689E−06 | 3.56985E−05 | 5.82918E−05 |
| 1.40537E−07 | 3.17257E−08 | 5.26642E−08 | 5.9355E−09 | 5.31491E−08 | 8.67868E−08 |
| 4.68458E−08 | 4.23009E−08 | 1.75547E−08 | 7.914E−09 | 5.31491E−08 | 2.89289E−07 |
| 4.21612E−07 | 9.5177E−08 | 1.57993E−07 | 1.78065E−08 | 1.59447E−07 | 2.6036E−07 |
| 2.34229E−07 | 1.58628E−07 | 3.51095E−07 | 5.9355E−08 | 7.97237E−07 | 1.59109E−06 |
| 4.68458E−08 | 1.05752E−08 | 1.75547E−08 | 1.9785E−09 | 1.77164E−08 | 2.89289E−08 |
| 0.000468458 | 0.000105752 | 0.000175547 | 0.000138495 | 0.00141731 | 0.000289289 |
| 0.000468458 | 0.000105752 | 0.000175547 | 3.957E−05 | 0.000531491 | 0.000289289 |
| 0.000468458 | 0.000105752 | 0.000175547 | 3.957E−05 | 0.000531491 | 0.000289289 |
| 0.000468458 | 0.000105752 | 0.000175547 | 3.957E−05 | 0.000531491 | 0.000289289 |
| 9.36916E−08 | 2.11505E−08 | 3.51095E−08 | 5.9355E−09 | 3.54328E−08 | 5.78579E−08 |
| 0 | 0 | 0 | 0 | 0 | 0 |
| 0.000936916 | 0.000211505 | 0.000351095 | 1.9785E−06 | 1.77164E−05 | 0.000578579 |
| 0.000468458 | 0.000105752 | 0.000175547 | 1.9785E−06 | 1.77164E−05 | 0.000289289 |
| 0.001873831 | 0.000423009 | 0.000702189 | 1.9785E−06 | 1.77164E−05 | 0.001157157 |
| 0.000468458 | 0.000105752 | 0.000175547 | 1.9785E−06 | 1.77164E−05 | 0.000289289 |
| 9.36916E−08 | 2.11505E−08 | 3.51095E−08 | 1.9785E−06 | 1.77164E−05 | 5.78579E−08 |
| 0 | 0 | 0 | 1.9785E−06 | 1.77164E−05 | 0 |
| 0.001405374 | 0.000528761 | 0.000526642 | 1.9785E−06 | 1.77164E−05 | 0.000867868 |
| 0.000468458 | 0.000423009 | 0.000175547 | 1.9785E−06 | 1.77164E−05 | 0.000289289 |
| 0.002342289 | 0.000105752 | 0.000877737 | 1.9785E−06 | 1.77164E−05 | 0.001446446 |
| 0.001873831 | 0.000105752 | 0.000702189 | 1.9785E−06 | 1.77164E−05 | 0.001157157 |
| 1.40537E−07 | 3.17257E−08 | 5.26642E−08 | 1.9785E−06 | 1.77164E−05 | 8.67868E−08 |
| 0 | 0 | 0 | 1.9785E−06 | 1.77164E−05 | 0 |
| 0.001873831 | 0.00095177 | 0.000702189 | 1.9785E−06 | 1.77164E−05 | 0.001157157 |
| 0.002810747 | 0.000528761 | 0.001053284 | 1.9785E−06 | 1.77164E−05 | 0.001735736 |
| 0.003279205 | 0.000105752 | 0.001228831 | 1.9785E−06 | 1.77164E−05 | 0.002025025 |
| 0.002342289 | 0.000105752 | 0.000877737 | 1.9785E−06 | 1.77164E−05 | 0.001446446 |
| 1.40537E−07 | 3.17257E−08 | 5.26642E−08 | 1.9785E−06 | 1.77164E−05 | 8.67868E−08 |
| 0 | 0 | 0 | 1.9785E−06 | 1.77164E−05 | 0 |
| 0.004647243 | 0.001049094 | 0.001741658 | 0.000196275 | 0.001757536 | 0.002870126 |
| 0 | 0 | 0 | 0 | 0 | 0 |
| 0.000468458 | 0.000105752 | 0.000175547 | 1.9785E−05 | 0.000177164 | 0.000289289 |
| 4.68458E−05 | 1.05752E−05 | 1.75547E−05 | 1.9785E−06 | 1.77164E−05 | 2.89289E−05 |
| 4.68458E−05 | 1.05752E−05 | 1.75547E−05 | 1.9785E−06 | 1.77164E−05 | 2.89289E−05 |
| 4.68458E−05 | 1.05752E−05 | 1.75547E−05 | 1.9785E−06 | 1.77164E−05 | 2.89289E−05 |
| 4.68458E−05 | 1.05752E−05 | 1.75547E−05 | 1.9785E−06 | 1.77164E−05 | 2.89289E−05 |
| 4.68458E−05 | 1.05752E−05 | 1.75547E−05 | 1.9785E−06 | 1.77164E−05 | 2.89289E−05 |
| 0.003326988 | 1.05752E−05 | 1.75547E−05 | 1.9785E−06 | 0.001293827 | 2.89289E−05 |
| 0 | 1.05752E−05 | 1.75547E−05 | 1.9785E−06 | 0 | 2.89289E−05 |

TABLE 4-continued

| 1 | 2 | 3 | 4 | 5 | 6 |
|---|---|---|---|---|---|
| 0.000936916 | 1.05752E-05 | 1.75547E-05 | 1.9785E-06 | 0.000354328 | 2.89289E-05 |
| 4.68458E-05 | 1.05752E-05 | 1.75547E-05 | 1.9785E-06 | 1.77164E-05 | 2.89289E-05 |
| 4.68458E-05 | 1.05752E-05 | 1.75547E-05 | 1.9785E-06 | 1.77164E-05 | 2.89289E-05 |
| 4.68458E-05 | 1.05752E-05 | 1.75547E-05 | 1.9785E-06 | 1.77164E-05 | 2.89289E-05 |
| 0.003747663 | 1.05752E-05 | 1.75547E-05 | 1.9785E-06 | 0.000531491 | 2.89289E-05 |
| 0.002810747 | 1.05752E-05 | 1.75547E-05 | 1.9785E-06 | 0.000531491 | 2.89289E-05 |
| 0.000468458 | 1.05752E-05 | 1.75547E-05 | 1.9785E-06 | 1.77164E-05 | 2.89289E-05 |
| 0.000468458 | 0.000105752 | 1.75547E-05 | 1.9785E-06 | 0.000365135 | 2.89289E-05 |
| 0.000468458 | 0.000105752 | 1.75547E-05 | 1.9785E-06 | 1.77164E-08 | 2.89289E-05 |
| 0.000468458 | 0.000105752 | 1.75547E-05 | 1.9785E-06 | 0.000177164 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 0.000531491 | 2.89289E-05 |
| 0.000468458 | 0.000105752 | 1.75547E-05 | 1.9785E-06 | 0.000531491 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |
| 0.000468458 | 0.000105752 | 1.75547E-05 | 1.9785E-06 | 1.77164E-05 | 2.89289E-05 |

TABLE 5

Comparison Data

| 1-5 | 2-5 | 3-5 | 4-5 | 5-6 |
|---|---|---|---|---|
| 0.999931494 | 0.999984536 | 0.999981301 | 0.999986296 | 0.999981135 |
| 1.3552E-07 | 6.1186E-08 | 5.0784E-08 | 1.71708E-08 | 2.05006E-07 |
| 1.3552E-07 | 3.0593E-08 | 5.0784E-08 | 5.72359E-09 | 1.02503E-07 |
| 2.39837E-06 | 5.41461E-07 | 8.98754E-07 | 1.01301E-07 | 9.07073E-07 |
| 1.3552E-07 | 3.0593E-08 | 5.0784E-08 | 5.72359E-09 | 5.12516E-08 |
| 1.3552E-07 | 3.0593E-08 | 5.0784E-08 | 5.72359E-09 | 5.12516E-08 |
| 1.3552E-07 | 3.0593E-08 | 5.0784E-08 | 5.72359E-09 | 5.12516E-08 |
| 0 | 0 | 0 | 0 | 5.12516E-08 |
| 0 | 0 | 0 | 0 | 0 |
| 1.4961E-07 | 3.37673E-08 | 5.6064E-08 | 6.31807E-09 | 5.65964E-08 |
| 5.50241E-09 | 1.24214E-09 | 2.06194E-09 | 2.31237E-10 | 2.08093E-09 |
| 1.21968E-14 | 2.75337E-15 | 4.57056E-15 | 5.15123E-16 | 4.61264E-15 |
| 1.3552E-14 | 1.22372E-14 | 5.0784E-15 | 2.28944E-15 | 1.53755E-14 |
| 1.09771E-13 | 2.47803E-14 | 4.1135E-14 | 4.63611E-15 | 4.15138E-14 |
| 3.7268E-13 | 2.52392E-13 | 5.58624E-13 | 9.44392E-14 | 1.26848E-12 |
| 1.3552E-15 | 3.0593E-16 | 5.0784E-16 | 5.72359E-17 | 5.12516E-16 |
| 1.3552E-07 | 3.0593E-08 | 5.0784E-08 | 4.00651E-08 | 4.10013E-07 |
| 1.3552E-07 | 3.0593E-08 | 5.0784E-08 | 1.14472E-08 | 1.53755E-07 |
| 1.3552E-07 | 3.0593E-08 | 5.0784E-08 | 1.14472E-08 | 1.53755E-07 |
| 1.3552E-07 | 3.0593E-08 | 5.0784E-08 | 1.14472E-08 | 1.53755E-07 |
| 5.42079E-15 | 1.22372E-15 | 2.03136E-15 | 3.43415E-16 | 2.05006E-15 |
| 0 | 0 | 0 | 0 | 0 |
| 5.42079E-07 | 1.22372E-07 | 2.03136E-07 | 1.14472E-09 | 1.02503E-08 |
| 1.3552E-07 | 3.0593E-08 | 5.0784E-08 | 5.72359E-10 | 5.12516E-09 |
| 2.16832E-06 | 4.89488E-07 | 8.12543E-07 | 2.28944E-09 | 2.05006E-08 |
| 1.3552E-07 | 3.0593E-08 | 5.0784E-08 | 5.72359E-10 | 5.12516E-09 |
| 5.42079E-15 | 1.22372E-15 | 2.03136E-15 | 1.14472E-13 | 1.02503E-12 |
| 0 | 0 | 0 | 0 | 0 |
| 1.21968E-06 | 4.58895E-07 | 4.57056E-07 | 1.71708E-09 | 1.53755E-08 |
| 1.3552E-07 | 1.22372E-07 | 5.0784E-08 | 5.72359E-10 | 5.12516E-09 |
| 3.388E-06 | 1.52965E-07 | 1.2696E-06 | 2.86179E-09 | 2.56258E-08 |
| 2.16832E-06 | 1.22372E-07 | 8.12543E-07 | 2.28944E-09 | 2.05006E-08 |
| 1.21968E-14 | 2.75337E-15 | 4.57056E-15 | 1.71708E-13 | 1.53755E-12 |
| 0 | 0 | 0 | 0 | 0 |
| 2.16832E-06 | 1.10135E-06 | 8.12543E-07 | 2.28944E-09 | 2.05006E-08 |
| 4.87871E-06 | 9.1779E-07 | 1.82822E-06 | 3.43415E-09 | 3.0751E-08 |
| 6.64047E-06 | 2.14151E-07 | 2.48841E-06 | 4.00651E-09 | 3.58761E-08 |
| 3.388E-06 | 1.52965E-07 | 1.2696E-06 | 2.86179E-09 | 2.56258E-08 |
| 1.21968E-14 | 2.75337E-15 | 4.57056E-15 | 1.71708E-13 | 1.53755E-12 |
| 0 | 0 | 0 | 0 | 0 |
| 1.33382E-05 | 3.01103E-06 | 4.99878E-06 | 5.63334E-07 | 5.04435E-06 |
| 0 | 0 | 0 | 0 | 0 |
| 1.3552E-07 | 3.0593E-08 | 5.0784E-08 | 5.72359E-09 | 5.12516E-08 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 9.62462E-08 | 3.0593E-10 | 5.0784E-10 | 5.72359E-11 | 3.7429E-08 |
| 0 | 3.0593E-10 | 5.0784E-10 | 5.72359E-11 | 0 |
| 2.7104E-08 | 3.0593E-10 | 5.0784E-10 | 5.72359E-11 | 1.02503E-08 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 1.3552E-09 | 3.0593E-10 | 5.0784E-10 | 5.72359E-11 | 5.12516E-10 |
| 1.08416E-07 | 3.0593E-10 | 5.0784E-10 | 5.72359E-11 | 1.53755E-08 |
| 8.13119E-08 | 3.0593E-10 | 5.0784E-10 | 5.72359E-11 | 1.53755E-08 |
| 1.3552E-08 | 3.0593E-10 | 5.0784E-10 | 5.72359E-11 | 5.12516E-10 |
| 1.3552E-08 | 3.0593E-09 | 5.0784E-10 | 5.72359E-11 | 1.0563E-08 |
| 1.3552E-08 | 3.0593E-09 | 5.0784E-10 | 5.72359E-11 | 5.12516E-13 |
| 1.3552E-08 | 3.0593E-09 | 5.0784E-10 | 5.72359E-11 | 5.12516E-09 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 1.53755E-08 |
| 1.3552E-08 | 3.0593E-09 | 5.0784E-10 | 5.72359E-11 | 1.53755E-08 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |
| 1.3552E-08 | 3.0593E-09 | 5.0784E-10 | 5.72359E-11 | 5.12516E-10 |

Dot Product

| 0.999976292 | 0.999992436 | 0.999997887 | 0.999987113 | 0.999988886 |

As shown in Table 5, the system is configured run a correlation algorithm, for example a Dot Product, on the normalized vector data, to identify with a high degree of probability [closest 1 to 1 correlation (1.0) for 1~6 to 1~5] that new patient (hit) 6 is the same patient as patient 3 in the historical vector data (1~6=0.999997887). In embodiments, the system can be configured tag correlated patients with an obfuscated identifier, which identifies the patient but is blind to the patient's identity.

As will be appreciated, an ordinarily skilled artisan informed by the teachings of the present specification can employ other correlation techniques, for example, maximum likelihood, distance formula, etc., on the super vectors as described herein to, inter alia, identify patients and other correlated vector dimension data. Further rules and filters can be applied to correlate data and treatment weights, for example distance rules (algorithm checks for x distance radius or area from location for same virtual patient) or exclusion rules (e.g.: rejects virtual hits from same provider on same date of service).

The system thereby provides technological platform and robust expert system for identifying, tracking and treating patients while protecting patient anonymity in de-identified databases. As will be appreciated, at least one technological advantage of the present system is it leverages existing data structures such as billing codes to address the need for patient anonymity while at the same time providing an information dense database for an expert patient care data system to run real-time algorithms on. The system is configured to transform billing data from each patient visit into a hit, and a patient will have multiple hits over their lifetime. The grouping of this disparate billing data will enable doctors to utilize this data to help real-time while treating their patients. The patient can be identified via a multidimensional correlation algorithm that employs parametric and non-parametric inputs. It identifies that most likely mapping and self-corrects based on absolute mapping requirements to determine whether an existing de-identified patients should be selected versus a generating a new de-identified patient.

The algorithms can be configured to, inter alia, to provide real time patient treatment that extant patient care expert systems as of the present disclosure, including predictive systems, cannot provide due to, inter alia, lack of relevant and robust data for patient identification, ailment correlation, and tracking that populate the dimensional data of the vectors and super vectors described herein.

In at least one of the various embodiments, information from patient/vector analysis component 510 may flow to report generator 516 and/or treatment and recommendation engine 518. For example, when a care provider enters a specific ailment for a patient, ICD and CPT codes are mapped to ailments, body parts and physical systems via the vector model as described herein. The treatment and recommendation engine 518 can be configured to retrieve data connected to the physical system selected by the doctor. A list of cases relating to that specific ailment generated, giving a care provider multiple cases of chosen ailment. The vector mapping component 508 and patient/vector analysis component 510 facilitates the system pulling this data together. The vector mapping makes the historical billing data (ICD and CPT data) actionable. As a care provider provides more specificity to physical systems that are most relevant to given task, the treatment/recommendation engine 518 is configured to return treatment data to a care provider GUI 520 to be utilized while treating patients in real time.

In at least one of the various embodiments, report generator 516 may be arranged to generate one or more reports based on the logged information. In at least one of the various embodiments, reports may include historical information or comparison information as well as performance information. For example, ailment searches can be saved and logged for CME credit, at the end of each month doctors or other care providers can receive log of search activity, which can be submitted for Continuing Education Credit, which is required per their licensing. In at least one of the various embodiments, reports may be determined and formatted based on one or more report templates.

In at least one of the various embodiments, care provider GUI 520 may render a display of the information produced by the other components of the systems. In at least one of the various embodiments, the type of information and/or the level of detail presented for the GUI may be determined based in part on the role of the target care provider user. In at least one of the various embodiments, care provider GUI display 520 may be presented on a client computer accessed over network, such as client computers 102, 103, 104, 105, 200, 412, 414, 416, 418, or the like. In at least one of the various embodiments, the care provider GUI is one or more of the event sources 502, 504, 506, for instance, where the care provider is providing vector data for a patient visit and the system is returning real-time treatment data via the treatment recommendation engine for that patient.

In various embodiments, disconnected diagnosis and billing data can be coalesced into a de-identified patient database, allowing users to link diagnoses and successful treatments.

In various embodiments, care providers on a worldwide basis can have access the treatment data and vector analysis data, which can be explored to assist with treatment and medical decision-making. Care providers in remote parts of the world can have access to first world information and thus improve global health care.

For example in an embodiment the system can configure the vectors such that: (1) symptoms can mapped to the most common current diagnoses and (2) diagnoses are mapped to the most common current treatment options (3) diagnosis and corresponding treatment can mapped to the most current outcome data; and (4) de-identified patient data from physicians using the expert medical system augments the database to continually improve statistical correlations for more accurate treatment outcome correlations. For example, event input which can be mapped to vector dimensions can include: Symptoms: ICD-9, ICD-10, Diagnoses: ICD-9, ICD-10; Treatments: CPT, medication prescription database (e.g., IMS Health); Geographic data; and Outcomes: (for example from Medicare or WHO data and databases). The comparator algorithms patient/vector analysis and recommendation engine can thereby include, for example, Diagnoses: ICD-9, ICD-1, Treatment: CPT, medication prescription database (e.g., IMS Health) and Outcomes.

Moreover, additional vectors can be created and added to the system based on other heath care coding systems, which can be dimensionalized and normalized for vector and super vector analysis as described herein.

In at least one of the various embodiments, the system can be configured to interact with or include a Medical Trading System. In at least one of the various embodiments, the system can be configured to allow care providers to offer one another surplus medicine, supplies and equipment as well as request needed medicine, supplies and equipment, including in developing regions, remote regions, and crisis zones. Algorithms can be configured to facilitate the trading of medicine, supplies, and equipment ensuring that the trades are fair, and that the developing world, remote regions and crisis zones are the main benefactors of this service. For example, in an embodiment, medical supply surpluses can be mapped to medical supply needs, and the relative value of mapped supplies can be determined by an algorithm that accounts for regional availability and local economic resources. Care providers can review lists of offerings and requests for trading opportunities. Inputs can include requests for medicines, non-medicine medical supplies and equipment. The system can be configured to provide offerings of medicines, non-medicine medical supplies and equipment. Both parties match potential trades together for review.

In at least one of the various embodiments, the Medical Trading System can be configured to provide staffing solutions for care providers. Care providers can volunteer time, which can be logged into the system and utilized in developing world remote regions and crisis zones. Job opportunities for doctors and other care providers can also be advertised on the site. The Medical Trading System and/or Medical Expert System can also include or configured to integrate with a social network system, where doctors will be able to network, seek mentorship and thus advance their careers through relationships built on the system. The system can be configured to link physicians or other care providers who want to volunteer in underserved areas with physicians in those areas. Area designations can be broad or specific. Physicians or other care providers can review lists of to find volunteer physicians or volunteer opportunities (e.g.: "Location: Quetzaltenango, Guatemala; Service: Pediatrician; Time: Sep. 5-Sep. 12, 2015. Languages: English, Spanish"). Inputs can include care provider postings wanting volunteer or employed positions and care provider postings needing volunteers or hires. The system can then be configured to output listing of positions sorted by type (volunteer vs. paid), timing, location, specialty, etc.

In at least one of the various embodiments, the Medical Trading System and/or Medical Expert System can be configured to provide training solutions for care providers. For example, advanced training options for doctors or other care providers can be provided by various Universities and Medical Institutions via the system. In an embodiment, the training can be offered via the system. Doctors and other care providers can be encouraged to trade training information on a global basis. In an embodiment, an algorithm can be configured for equitable training trades. In at least one of the various embodiments, the system can include training trades for care providers, and open message boards and queries with ongoing streams/themes. For example, an exemplary trade can be a four-day trade seminar where spine surgeons and acupuncturists trade minimally invasive microdiscectomy and acupuncture techniques for the treatment of herniated lumbar discs. The system can be configured to allow care providers to input skill sets and desired training opportunities, and the system can output listings of potential trade matches.

Generalized Operation

The operation of certain aspects of the invention will now be described with respect to FIGS. 6-8. In at least one of various embodiments, processes 600, 700, 800 described in conjunction with FIGS. 6-8, respectively, may be implemented by and/or executed on a single network computer, such as network computer 300 of FIG. 3. In other embodiments, these processes or portions of these processes may be implemented by and/or executed on a plurality of network computers, such as network computer 300 of FIG. 3. Likewise, in at least one of the various embodiments, processes 600, 700, 800 or portions thereof, may be operative on one or more client computers, such as client computer 200 of FIG. 2. However, embodiments are not so limited, and various combinations of network computers, client computers, virtual machines, or the like may be utilized. Further, in at least one of the various embodiments, the processes described in conjunction with FIGS. 6-8 may be operative in system with logical architectures such as those described in conjunction with FIGS. 4-5.

In various implementations, a real-time, network-based, collaborative patient treatment guide is provided, comprising: receiving patient billing data at a network processor from a multitude of care providers located worldwide; mapping the patient billing data to an anonymous patient database, the patient billing data including billing codes and de-identified patient data; transforming the billing codes and the patient data into multidimensional vectors; analyzing the multidimensional vectors to correlate diagnoses, treatment regimens, and treatment results with ailments of human anatomy, physiology, and psychology; and returning a real-time, network-based, collaborative patient treatment guide to at least a subset of the multitude of care providers, based on the analyzing.

In an implementation, the transforming includes: accessing an entry of billing data having multiple data fields; mapping each of the data fields to an integer value; and forming a multidimensional vector representing the entry of billing data using each integer value of each data field of the entry of billing data to provide a magnitude component and a direction component to the multidimensional vector. In an example, determining the integer value of a data field is based on a diagnostic code or a patient code associated to the data field as discussed herein.

In an implementation, the process includes forming a super-vector from two or more multidimensional vectors, the super-vector having magnitude and direction components based on the two or more multidimensional vectors. The process further includes analyzing multiple super-vectors and correlating diagnoses, treatment regimens, and treatment results with ailments of human anatomy, physiology, and psychology; and returning the real-time, network-based, collaborative patient treatment guide to at least a subset of the multitude of care providers, based on the correlating.

FIG. 6 illustrates an overview flowchart for process 600 for treating a patient in accordance with at least one of the various embodiments. In an example, the process 600 includes receiving an input selection of a physical system of human anatomy from a networked care provider via a user interface; displaying a set of ailments related to the physical system at the user interface, based on the input selection and collected historical data; receiving an input selection of an ailment of the set of ailments; retrieving treatment data associated to the ailment in response to the input selection of the ailment, the treatment data including diagnoses, treatment regimens, and treatment results; and displaying the treatment data via the user interface. In one embodiment, the process includes receiving one or more input selections of a system of human anatomy, physiology, or psychology; and displaying treatment data associated to the one or more input selections.

In an implementation, the process includes saving search data including one or more input selections at the processor for later retrieval. In another implementation, the process includes providing a log of input selections and search results to a user via the user interface.

As described herein, the system makes use of collected data. In one example, the process includes collecting historical data including records of ailments associated to systems of human anatomy, physiology, or psychology. In another example, the process includes collecting historical data including records of diagnoses, proposed treatments, actual treatments, and treatment results regarding ailments associated to a system of human anatomy, physiology, or psychology.

Figure 9:
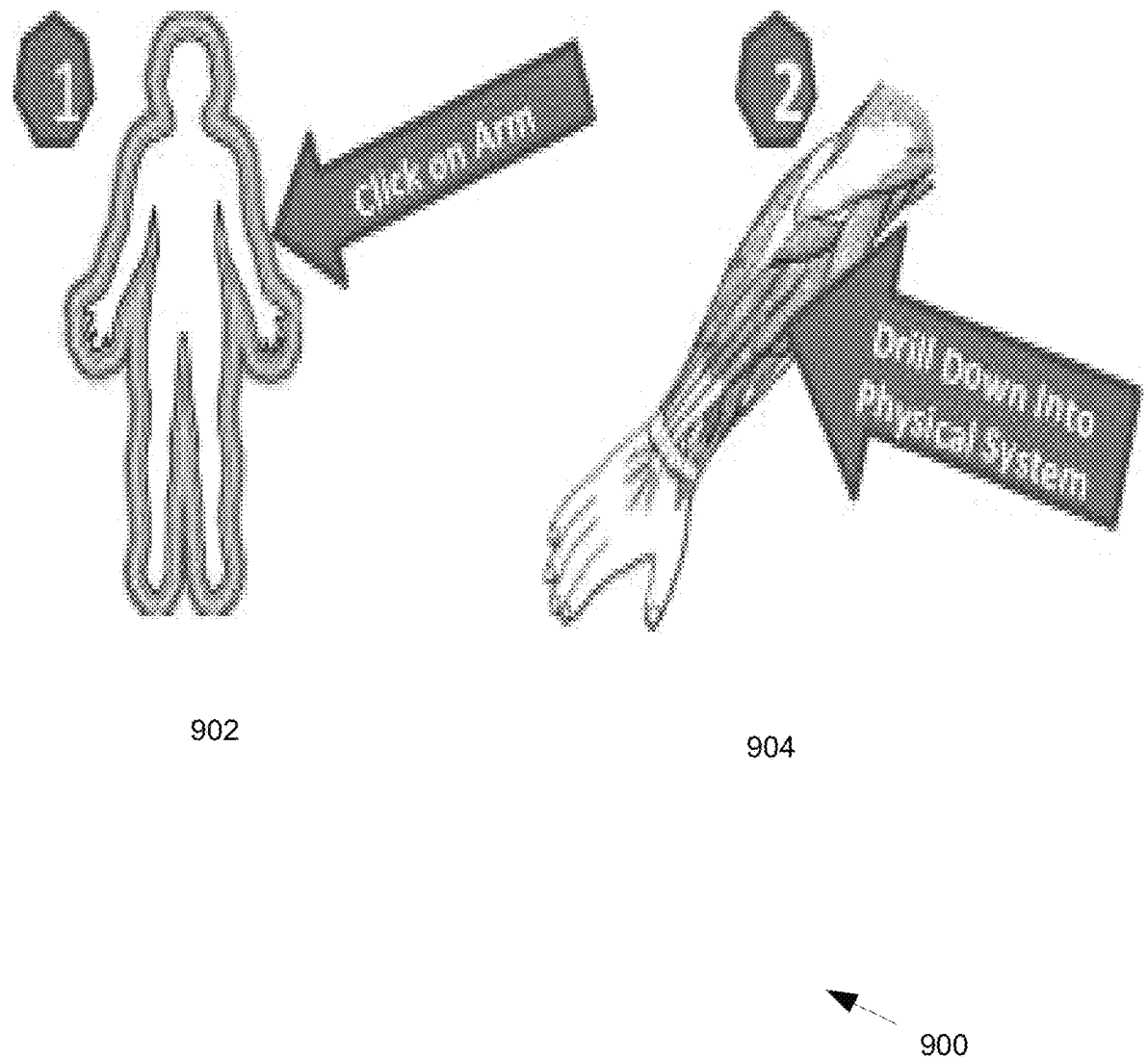
FIG. 9 shows a user interface element in accordance with at least one of the various embodiments.

Referring to FIG. 6, in an example, after a start block at block 602, in at least one of the various embodiments, at block 604 a care provider selects a physical system from via a system interface, for example a care provider GUI. An exemplary GUI physical system interface element is shown at FIG. 9, which shows an interactive graphic of a human body. The system can be configured to allow the care provider to select a gross physical system 902 and continue to drill down into the selected parts 904 until reaching a relevant system for a patient.

In at least one of the various embodiments, at block 608, the system is configured to provide a list of ailments for the selected physical system, which the care provider selects an ailment from at block 610. In at least one of the various embodiments, at block 612, the system can be configured to retrieve data connected to the physical system selected by the doctor. In at least one of the various embodiments, at block 614, the system is configured to provide a list of cases relating to that specific ailment selected, giving a care provider multiple cases of chosen ailment. In at least one of the various embodiments, the vector mapping component and patient/vector analysis components described herein facilitates the system pulling this data together and providing it to the care provider, for example via the treatment engine.

In at least one of the various embodiments, as a care provider provides more specificity to physical systems that are most relevant to given task, at block 618 the treatment/recommendation engine is configured to return treatment data to a care provider, for example via a GUI to be utilized while treating patients in real time. In at least one of the various embodiments, event information from the care provider may be stored in one or more databases, for later processing and/or analysis as described herein. Likewise, in at least one of the various embodiments, event information may be processed as it is determined or received. Also, event information may be stored in data stores, such as databases, for use as historical information and/or comparison information. In at least one of the various embodiments, at block 620 the system is configured to save search data and at block 622, the system can be configured to provide reports and logs to the care provider.

Figure 7:
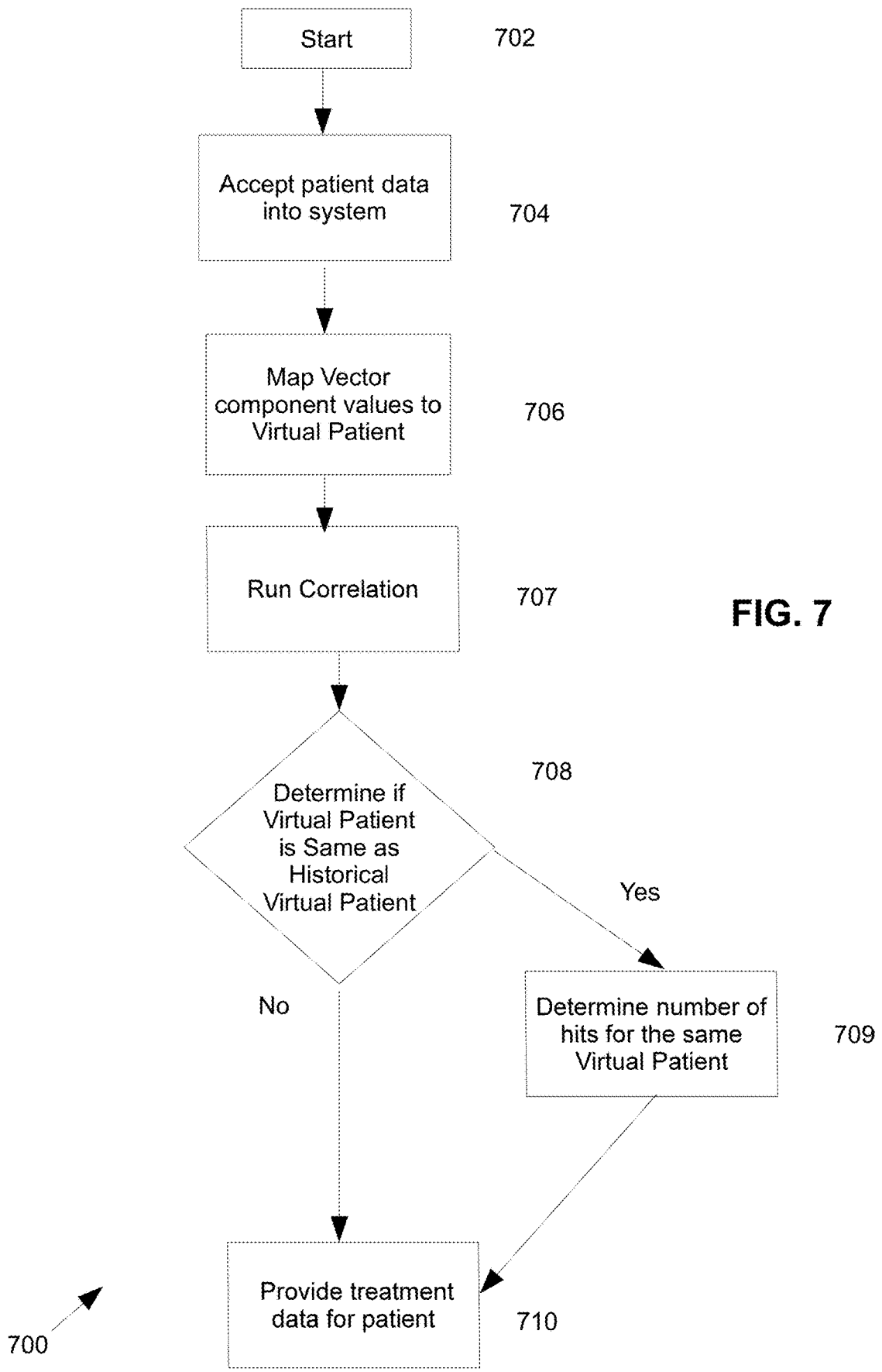
FIG. 7 illustrates a flowchart for a process in accordance with at least one of the various embodiments.

FIG. 7 illustrates an overview flowchart for process 700 for identifying and providing treating data for a patient in accordance with at least one of the various embodiments. For example, in an embodiment, the process includes receiving a new entry of patient billing data associated with an identified patient; mapping and transforming the new entry of patient billing data to form a new multidimensional vector; correlating the new vector to historical vectors of the anonymous patient database; determining whether any of the historical vectors correspond to the new vector or the identified patient; and returning treatment data for the identified patient based on the new vector and any historical vectors corresponding to the new vector or the identified patient.

Referring to FIG. 7, in an example, after a start block 702, in at least one of the various embodiments, at block 704 the system is configured to accept data into the system for a patient from a care provider.

At block 706, in at least one of the various embodiments, the system maps vector component values, for example to a super vector, representing a virtual patient visit. As noted herein, the patient treatment system accepts de-identified data, thus the actual identity of the patient is obfuscated, and hence referred to as a virtual patient. Exemplary mapping is described herein with respect to FIGS. 5A-5F and FIG. 8.

At block 707, in at least one of the various embodiments, the system is configured to process and compare super vector data for the virtual patient with historical super vector data for cases and run a comparator including one or more comparator algorithms and filters or rules to identify that the virtual patient is the same as a prior virtual patient. Exemplary comparators are described herein with respect to FIGS. 5A-5F and 8.

By running the comparator, at block 708, in at least one of the various embodiments, the system is configured to determine if a virtual patient is the same as a historical virtual patient with a high degree of certainty. An example of such determination is described with FIGS. 5A-F and Table 5.

At block 709, in at least one of the various embodiments, if the virtual patient is the same as a historical virtual patient, in at least one of the various embodiments, the system is configured to determine the number of prior case visits, or hits, for the identified virtual patient.

At block 710, in at least one of the various embodiments, the system is configured to provide treatment data for the patient. If the system did not identify a historical virtual patient as the same patient at block 708, the system is configured to provide treatment data based on the ailment and physical system selected by a care provider and any correlated diagnostic and outcome data as described herein. The system also logs and saves the virtual patient data, including super vector data, a database as historical data, which allows the system to track the patient throughout the patient's lifetime using the system.

Figure 8:
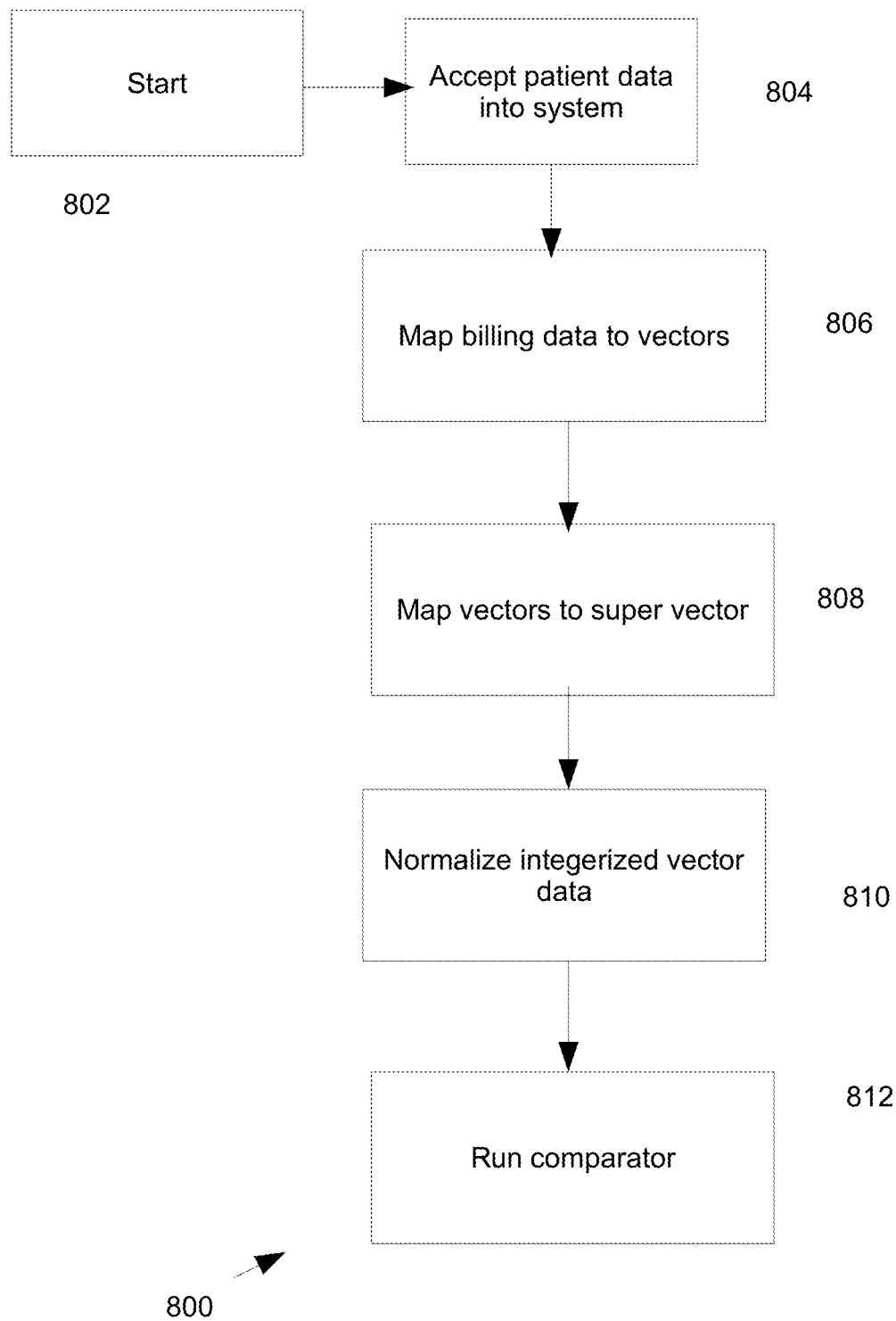
FIG. 8 illustrates a flowchart for a process in accordance with at least one of the various embodiments.

FIG. 8 illustrates an overview flowchart for process 800 for ingesting billing and patient data and correlating it to vectors for correlation. After a start block 802, in at least one of the various embodiments, at block 804 the system is configured to accept billing data into the system. Raw or processed billing data can be provided by care provider servers or client computers. In embodiments, data can also be provided by billing data stores and servers, for example, data is stored and accessible via the web in databases at the Centers for Medicare & Medicaid Services (CMS) <ww.cms.gov> or sources employing or warehousing other billing code systems (e.g. from other jurisdictions, entities, agencies charged with managing billing information, insurance companies, etc.).

At block 806 the system is configured to map billing data to vectors as described herein with respect to, inter alia, FIGS. 5A-F and Tables 2-3.

At block 808, in at least one of the various embodiments, the system is configured to provide map vector data for each patient visit to a super vector. An example of mapping billing data is described herein with respect to, inter alia, Table 3.

At block 810, in at least one of the various embodiments, the system is configured to normalize the mapped intergerized vector data of the supervectors. For an example, the integer vector data of Table 3 produces the normalized data as shown in Table 4.

At block 812, in at least one of the various embodiments, the system is configured to run one or more comparator including correlation algorithms to correlate supervectors for patient and treatment data. An example of mapping billing data is described herein with respect to Table 5.

It will be understood that the each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system or even a group of multiple computer systems. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware-based systems, which perform the specified actions or steps, or combinations of special purpose hardware and computer instructions. The foregoing example should not be construed as limiting and/or exhaustive, but rather, an illustrative use case to show an implementation of at least one of the various embodiments of the invention.

What is claimed is:

1. A network-based, collaborative, medical expert system, comprising:
   a processor coupled to a network;
   memory coupled to the processor;
   an analysis component stored in the memory and operable on the processor to:
      receive, from a multitude of care providers worldwide, a plurality of data including patient billing data, provider data, and time data associated with a plurality of patient visits;
      map at least the patient billing data to an anonymous patient database, the patient billing data including billing codes and de-identified patient data;
      transform the billing data into multidimensional billing vectors, the provider data into multidimensional provider vectors, and the time data into multidimensional time vectors;
      form a super-vector from a multidimensional billing vector, a multidimensional provider vector, and a multidimensional time vector each associated with a same patient visit, said super-vector associated with a de-identified patient and comprising a plurality of dimensions; and
      determining an identity associated with the de-identified patient, wherein determining the identity comprises:
         mapping each of the plurality of dimensions of the super-vector and each of a plurality of dimensions of the historical super-vector to respective integer values;
         normalizing each respective integer value for each of the plurality of dimensions of the super-vector and each of the plurality of dimensions of the historical super-vector;
         comparing each of the plurality of dimensions of the super-vector to a respective dimension of a historical super-vector associated with a correlated patient;
         identifying a match between the correlated patient and the de-identified patient as a function of the comparison; and
         determining the identity of the de-identified patient to be the same as the correlated patient as a function of the identified match;
      analyze the super-vector to correlate diagnoses, treatment regimens, and treatment results with ailments of human anatomy, physiology, and psychology; and
   a network communication component coupled to the processor and adapted to return a real-time, network-based, collaborative patient treatment guide to a user interface of at least a subset of the multitude of care providers, based on a continuous real-time receipt of patient billing data, transformation of the billing data, and analysis of the multidimensional vectors.

2. The system of claim 1, wherein:
   the patient billing data is stored in the plurality of dimensions of the super-vector; and
   the analysis component is further adapted to:
      map each of the dimensions of the super-vector to an integer value, whereby the super-vector has a magnitude component and a direction component formed using the integer value of each dimension of the patient billing data.

3. The system of claim 2, wherein the integer value of each dimension is determined based on a diagnostic code or a patient code of the dimension.

4. The system of claim 1, wherein the analysis component is adapted to provide a care provider with access to the treatment guide to retrieve diagnostic data in real-time, and wherein the analysis component is configured to identify and to provide treatment solutions for a virtual patient via a multidimensional correlation algorithm employing parametric and non-parametric inputs.

5. The system of claim 1, wherein the analysis component is adapted to identify the most likely patient billing data mapping, and to correct a mapping based on whether an existing de-identified patient is associated to the mapping or whether a new de-identified patient is generated and associated to the mapping.

6. The system of claim 1, wherein the analysis component is adapted to process diagnosis and billing data into the anonymous patient database, wherein the analysis component is configured to allow a care provider to link diagnoses and successful treatments.

7. The system of claim 1, wherein comparing each of the plurality of dimensions to a respective dimension of the historical super-vector comprises:
   comparing each respective normalized value for each of the plurality of dimensions of the super-vector to a respective normalized value for a respective dimension of the historical super-vector.

8. The system of claim 7, wherein identifying a match between the correlated patient and the de-identified patient further comprises executing a dot product.

9. A method of providing a real-time, network-based, collaborative patient treatment guide, comprising:
   receiving, from a multitude of care providers worldwide, a plurality of data including patient billing data, provider data, and time data associated with a plurality of patient visits at a network processor;

mapping at least the patient billing data to an anonymous patient database, the patient billing data including billing codes and de-identified patient data;
transforming the billing data into multidimensional billing vectors, the provider data into multidimensional provider vectors, and the time data into multidimensional time vectors;
combining a multidimensional billing vector, a multidimensional provider vector, and a multidimensional time vector each associated with a same patient visit to form a super-vector, said super-vector associated with a de-identified patient and comprising a plurality of dimensions;
determining an identity associated with the de-identified patient, wherein determining the identity comprises:
mapping each of the plurality of dimensions of the super-vector and each of a plurality of dimensions of the historical super-vector to respective integer values;
normalizing each respective integer value for each of the plurality of dimensions of the super-vector and each of the plurality of dimensions of the historical super-vector;
comparing each of the plurality of dimensions of the super-vector to a respective dimension of a historical super-vector associated with a correlated patient;
identifying a match between the correlated patient and the de-identified patient as a function of the comparison; and
determining the identity of the de-identified patient to be the same as the correlated patient as a function of the identified match;
analyzing the super-vector to correlate diagnoses, treatment regimens, and treatment results with ailments of human anatomy, physiology, and psychology; and
returning a real-time, network-based, collaborative patient treatment guide to at least a subset of the multitude of care providers, based on the analyzing.

10. The method of claim 9, wherein:
the step of transforming, further includes:
accessing an entry of billing data having multiple data fields; mapping each of the data fields to an integer value; and
forming a multidimensional vector representing the entry of billing data using each integer value of each data field of the entry of billing data to provide a magnitude component and a direction component to the multidimensional vector; and
the step of combining two or more of the multidimensional vectors to form a super-vector further comprises providing super-vector magnitude and a super-vector direction components based on the two or more multidimensional vectors.

11. The method of claim 10, wherein the step of transforming further comprises determining the integer value of each data field based on a diagnostic code or a patient code associated to the data field.

12. The method of claim 9, further comprising analyzing multiple super-vectors and correlating diagnoses, treatment regimens, and treatment results with ailments of human anatomy, physiology, and psychology; and returning the real-time, network-based, collaborative patient treatment guide to at least a subset of the multitude of care providers, based on the correlating.

13. The method of claim 9, further comprising:
receiving an input selection of a physical system of human anatomy from a networked care provider via a user interface;
displaying a set of ailments related to the physical system at the user interface, based on the input selection and collected historical data;
receiving an input selection of an ailment of the set of ailments;
retrieving treatment data associated to the ailment in response to the input selection of the ailment, the treatment data including diagnoses, treatment regimens, and treatment results; and
displaying the treatment data via the user interface.

14. The method of claim 13, further comprising receiving one or more input selections of a system of human anatomy, physiology, or psychology; and
displaying treatment data associated to the one or more input selections.

15. The method of claim 13, further comprising saving search data including one or more input selections at the processor for later retrieval.

16. The method of claim 13, further comprising providing a log of input selections and search results to a user via the user interface.

17. The method of claim 9, further comprising collecting historical data including records of ailments associated to systems of human anatomy, physiology, or psychology.

18. The method of claim 9, further comprising collecting historical data including records of diagnoses, proposed treatments, actual treatments, and treatment results regarding ailments associated to a system of human anatomy, physiology, or psychology.

19. The method of claim 9, further comprising:
storing the super-vector to the anonymous patient database as a historical super-vector within a plurality of historical super-vectors;
receiving a new entry of patient billing data associated with an identified patient;
mapping and transforming the new entry of patient billing data to form a new super-vector;
correlating the new super-vector to the plurality of historical super-vectors of the anonymous patient database;
determining whether any of the plurality of historical super-vectors correspond to the new super-vector or the identified patient; and
returning treatment data for the identified patient based on the new super-vector and any historical super-vectors corresponding to the new super-vector or the identified patient.

* * * * *